United States Patent
Goodyear et al.

(10) Patent No.: US 10,632,175 B2
(45) Date of Patent: Apr. 28, 2020

(54) EXERCISE-REGULATED ADIPOKINES AS THERAPY FOR DIABETES MANAGEMENT

(71) Applicant: Joslin Diabetes Center, Inc., Boston, MA (US)

(72) Inventors: Laurie J. Goodyear, Southborough, MA (US); Kristin I. Stanford, Roslindale, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

(21) Appl. No.: 14/771,677

(22) PCT Filed: Mar. 4, 2014

(86) PCT No.: PCT/US2014/020170
§ 371 (c)(1),
(2) Date: Aug. 31, 2015

(87) PCT Pub. No.: WO2014/137997
PCT Pub. Date: Sep. 12, 2014

(65) Prior Publication Data
US 2016/0000872 A1    Jan. 7, 2016

Related U.S. Application Data

(60) Provisional application No. 61/772,296, filed on Mar. 4, 2013.

(51) Int. Cl.
*A61K 38/18* (2006.01)
*A61K 38/17* (2006.01)

(52) U.S. Cl.
CPC ...... *A61K 38/1841* (2013.01); *A61K 38/1709* (2013.01)

(58) Field of Classification Search
None
See application file for complete search history.

(56) References Cited

U.S. PATENT DOCUMENTS 8,202,966 B2 *   6/2012   McCarthy .............. C07K 14/47
                                                              435/7.2
2003/0215836 A1   11/2003  Young et al.
2005/0187154 A1    8/2005  Kahn et al.
2006/0223104 A1   10/2006  Kahn et al.
2010/0267576 A1 * 10/2010  Zhang .................. C12Q 1/6883
                                                              506/9

FOREIGN PATENT DOCUMENTS

WO    2008083330 A2    7/2008
WO    2012162392 A1   11/2012

OTHER PUBLICATIONS

Blood Glucose Testing-Diabetes info NZ (available online Feb. 1, 2001).*
Healthline-Glucose Tolerance Test (Sep. 28, 2012).*
(NIH, Genetics Home Reference; < https://ghr.nlm.nih.gov/gene/TGFB2> 2018).*
(https://www.ncbi.nlm.nih.gov/gene/167 Oct. 2018).*
(https://www.ncbi.nlm.nih.gov/gene/63827 Nov. 2018).*
Sigal, et al. "Physical Activity/Exercise and Type 2 Diabetes" Diabetes Care; Oct. 2004; vol. 27; No. 10; pp. 2518-2539.
Tran, et al. "Beneficial Effects of Subcutaneous Fat Transplantation on Metabolism" Cell Metab.; May 2008; vol. 7; No. 5; pp. 410-420.
Brandt, et al. "The Role of Exercise-Induced Myokines in Muscle Homeostasis and the Defense against Chronic Diseases" Journal of Biomedicine and Biotechnology; e-published Mar. 9, 2010; Article ID 520258; 6 pages.
Kourtoglou "Insulin therapy and exercise" Diabetes Research and Clinical Practice; Aug. 2011; 93 Suppl 1; pp. S73-S77.
Goodyear, et al. "Exercise, Glucose Transport, and Insulin Sensitivity" Annu. Rev. Med.; 1998; vol. 49; pp. 235-261.

* cited by examiner

*Primary Examiner* — James H Alstrum-Acevedo
*Assistant Examiner* — Tara L Martinez
(74) *Attorney, Agent, or Firm* — Pierce Atwood LLP; Kevin M. Farrell; Stephanie Westcot

(57) ABSTRACT

The present invention is related to methods and compositions effective in regulating glycemic control in subject individuals in need of the regulation of glycemic control. Said individuals may have diabetes or be prediabetic condition receive therapeutically effective amounts of identified secreted proteins in an amount suitable for modulating glycemic control and to thereby treat or prevent diabetes in said subject.

10 Claims, 14 Drawing Sheets

FIG. 2A

| | List of Up-Regulated Secreted Proteins from Trained scWAT | | | | | | | | |
|---|---|---|---|---|---|---|---|---|---|
| No. | Protein | Gene Name | Fold Increase | Putative/Established Function | Putative/ Established Disease Association | Established Adipokine | Receptor | Receptor Location | Comments |
| 1 | wingless-related MMTV integration site 3 | Wnt3 | 3.82 | Required for primary axis formation in the mouse. May play a role in some cases of human breast, rectal, lung, and gastric cancer through activation of the WNT-beta-catenin-TCF signaling pathway. Incubation of EMSC adipocytes with Wnt3a for 48 hours increased OCR and mitochondrial genes. | Cancer, Aging | | lin-44 (nematodes) | neuron | Largest increase of secreted proteins and highly significant in mouse. In humans, exercise training increases other WNT family members including 4, 5A, 6, and 7B. Recently, there has been considerable interest in Wnt and Sfrp proteins in adipose biology, especially adipogenesis. |
| 2 | NEL-like 2 | NELL2 | 2.62 | Glycoprotein containing several EGF-like domains. Plays a role in neural cell growth and differentiation as well as in oncogenesis. | Cancer | | | | Relatively low expression in adipose (visceral?). |
| 3 | nephronectin | NPNT | 2.49 | Ligand for the integrin α8β1. Contains 5 EGF-like domains. A cell matrix protein involved in cell matrix adhesion. Necessary for muscle cell fusion. | Diabetic Glomerulosclerosis | | | | ubiquitous expression |
| 4 | cysteine rich protein 61 | CYR61 | 2.25 | Cell proliferation, differentiation, angiogenesis, apoptosis, and extracellular matrix formation. | unknown | yes | Integrin family | Monocyte, bone | CYR61 polymorphisms are associated with plasma HDL levels in obesity. Reasonably high expression in adipose tissue. |
| 5 | apolipoprotein A-V | APOA5 | 2.21 | Triglyceride transport. | CAD, Dyslipidemia | | | | |
| 6 | brevican | BCAN | 2.19 | Invasion, motility, adhesion, cell growth. | Cancer, Stroke | | | | |
| 7 | chemokine (C-C motif) ligand 25 | CCL25 | 2.19 | Inflammation, cancer invasion. | Cancer, Crohn's disease | | CCR9 | Thymus, Leukemia lymphoblast | |

FIG. 2B

| No. | Protein | Gene Name | Fold Increase | Putative/Established Function | Putative/Established Disease Association | Established Adipokine | Receptor | Receptor Location | Comments |
|---|---|---|---|---|---|---|---|---|---|
| 8 | paraoxonase 1 | PON1 | 2.18 | Attaches to high density lipoproteins (HDL) particles in serum and plays a crucial role in inhibiting prooxidative damage and LDL oxidation | CAD, Alzheimers, Diabetes | | | | |
| 9 | prolactin induced protein | PIP | 2.08 | Expressed in begine and malignant human breast tumors and in such normal exocrine organs as sweat, salivary and lacrimal glands. | Breast Cancer, Prostate Cancer | | | | |
| 10 | hyaluronan and proteoglycan link pro | HAPLN1 | 1.99 | Cell adhesion, skeletal muscle development. | Diabetes, Obesity | | | | |
| 11 | angiopoietin-like 2 | ANGPTL2 | 1.91 | Improves insulin resistance in adipocytes. | Diabetes | yes | | | |
| 12 | alpha-2-glycoprotein 1, zinc | AZGP | 1.88 | Lipid metabolism, insulin resistance. | Obesity | yes | | | |
| 13 | corticotropin releasing hormone binding protein | CRHBP | 1.87 | Related to stress in alcoholism. Increase throughout pregnancy and falls rapidly after parturition. | Alcoholism, Pregnancy | | | | |
| 14 | serine (or cysteine) peptidase inhibitor, clade A (alpha-1 antiproteinase, antitrypsin), member 12 (vaspin) | SERPINA | 1.86 | Alpha-1 antitrypsin (AAT) is the proteolytic member of the serine protease inhibitor (serpin) superfamily of proteins, which has a major role in inactivating neutrophil elastase and other proteases to maintain protease-antiprotease balance. | Emphysema, Liver disease, Diabetes | yes | | | |
| 15 | apolipoprotein A-IV | APOA4 | 1.86 | A potent activator of lecithin-cholesterol acyltransferase in vitro. | Dyslipidemia | | | | |
| 16 | cysteine-rich secretory protein 1 | CRISP1 | 1.85 | Involved in sperm-egg plasma membrane fusion. | | | | | |
| 17 | a disintegrin-like and metallopeptidase (reprolysin type) with thrombospondin type 1 motif. | ADAMTS1 | 1.85 | Inflammation, coagulation, anti-tumor growth | Knobloch syndrome | yes | | | |
| 18 | apolipoprotein M | APOM | 1.82 | Associated with high density lipoproteins and to a lesser extent with low density lipoproteins and triglyceride-rich lipoproteins. | Dyslipidemia | | | | |

FIG. 2C

| No. | Protein | Gene Name | Fold Increase | Putative/Established Function | Putative/Established Disease Association | Established Adipokine | Receptor | Receptor Location | Comments |
|---|---|---|---|---|---|---|---|---|---|
| 19 | chemokine (C-X-C motif) ligand 15 | CXCL15 | 1.79 | Inflammation | Unknown | | | | |
| 20 | dickkopf homolog 2 (Xenopus laevis) | DKK2 | 1.74 | Angiogenesis, cell growth | Cancer | | transmembrane proteins Kremen1 and -2 | fibroblasts | |
| 21 | apolipoprotein C-III | APOC3 | 1.67 | Increase in apoC-III levels induces the development of hypertriglyceridemia. | Dyslipidemia, Fatty liver | | | | |
| 22 | phospholipase A2, group IIF | PLA2G2F | 1.66 | Catalyzes the release of fatty acids from glycero-3-phosphocholines. The best known varieties are the digestive enzymes secreted as zymogens by the pancreas of mammals. | | | | | |
| 23 | collagen, type XI, alpha 2 | COL11A2 | 1.61 | One of the two alpha chains of type XI collagen, a minor fibrillar collagen | type III Stickler syndrome, Vasculitis | fm | | | |
| 24 | fibroblast growth factor 5 | FGF5 | 1.54 | Cell growth, morphogenesis, tissue repair, tumor growth and invasion. | | yes | FGFR1,2,3,4,5 | ubiquitous | |
| 25 | tissue inhibitor of metalloproteinase 3 | TIMP3 | 1.48 | Anti-TNFa. Involved in apoptosis, growth, invasion, proliferation, malignancy, quantity, cell-cell adhesion, morphology, tubulation, migration. | Cancer | | | | |
| 26 | growth arrest specific 6 | GAS6 | 1.46 | Inflammation, stimulation of cell proliferation, thrombosis, adipocyte development | Diabetes, Liver injury, Obesity | yes | Tyro3, Mer, Axl | ubiquitous | |
| 27 | insulin-like growth factor binding protein 5 | IGFBP5 | 1.46 | Mesenchymal progenitor cell proliferation, differentiation and migration | Cancer, Obesity | yes | | | |
| 28 | phospholipase A2, group IB, pancreas | PLA2G1B | 1.44 | Catalyzes the release of fatty acids from glycero-3-phosphocholines. | Diabetes | | PLA2R1 | ubiquitous | |

FIG. 2D

| No. | Protein | Gene Name | Fold Increase | Putative/Established Function | Putative/Established Disease Association | Established Adipokine | Receptor | Receptor Location | Comments |
|---|---|---|---|---|---|---|---|---|---|
| 29 | vascular endothelial growth factor A | VEGFA | 1.44 | Functions in physiological and pathological angiogenesis through the increase of proliferation and migration of endothelial cells | Obesity, Cancer | yes | VEGFR1 (Flt1), VEGFR2(KDR) | ubiquitous | |
| 30 | superoxide dismutase 1, soluble | SOD1 | 1.43 | Binds copper and zinc ions and is one of two isozymes responsible for destroying free superoxide radicals in the body. | Diabetes | yes | IRE1 ?, PERK ? | nuron | |
| 31 | leucine-rich repeat LGI family, member 1 | LGI1 | 1.42 | Mutation described in patient with autosomal dominant partial epilepsy with auditory features (ADPEAF), and recent clinical findings have implicated LGI1 in human brain development. | Epilepsy | yes | ADAM22 | ubiquitous | |
| 32 | serine (or cysteine) peptidase inhibitor, clade 1, member 2 | SERPINI2 | 1.42 | Coagulation, fibrinolysis, development, malignancy and inflammation. | Cancer | yes | | | |
| 33 | protease, serine, 2 | Prss2 | 1.41 | The androgen-controlled prostate specific gene, transmembrane protease serine 2, fused to members of the erythroblastosis virus E26 transforming sequence family of transcription factors, most notably ERG, leading to the overexpression of oncogenic transcription factors. | Prostate Cancer | | | | |
| 34 | pancreatic lipase | PNLIP | 1.40 | Hydrolyzes insoluble, emulsified triglycerides, and is essential for the efficient digestion of dietary fats. | | | | | |
| 35 | lipase, hormone sensitive | LIPE | 1.40 | Hydrolyzes stored triglycerides to free fatty acids. | Diabetes | | perilipin (regulator of LIPE in lipid, non-receptor) | Adipocyte | |

FIG. 2E

| No. | Protein | Gene Name | Fold Increase | Putative/Established Function | Putative/Established Disease Association | Established Adipokine | Receptor | Receptor Location | Comments |
|---|---|---|---|---|---|---|---|---|---|
| 36 | chemokine (C-X-C motif) ligand 12 | CXCL12 | 1.39 | Inflamation, Cancer metastasis, NASH | Cancer (Breast), NASH | | CXCR4 | Bone marrow, WBC | |
| 37 | anti-Mullerian hormone | AMH | 1.38 | A member of the transforming growth factor-beta gene family which mediates male sexual differentiation. | Colon Cancer, Mullerian Duct Syndrome | | AMHR2 | ubiquitous | |
| 38 | amyloid beta (A4) precursor-like protein 2 | APLP2 | 1.35 | Required to mediate neuromuscular transmission, spatial learning and synaptic plasticity. | Alzheimers | | | | |
| 39 | glutathione peroxidase 3 | GPX3 | 1.34 | Anti-oxidant, anti-cancer enzyme. | Cancer, Stroke | yes | | | |
| 40 | lysyl oxidase-like 1 | LOXL1 | 1.34 | Biogenesis of connective tissue, encoding an extracellular copper-dependent amine oxidase. | Glaucoma, Alzheimers | yes | | | |
| 41 | apolipoprotein C-1 | APOC1 | 1.34 | On HDL, protective for HDL. On TG rich lipoprotein, clearance is decreased. | CAD, Dyslipidemia | tm | | | |
| 42 | neurotrophin 3 | NTF3 | 1.33 | Maintenance of the adult nervous system, and may affect development of neurons in the embryo. | Alzheimers | | NTRK1,2,3 | ubiquitous | |
| 43 | cardiotrophin 1 | CTF1 | 1.32 | IL6 family, cardiomyocyte growth, hepatocyte protection and regeneration. | Metabolic Syndrome | | glycoprotein 130 (interleukin 6 signal transducer) | ubiquitous | |
| 44 | platelet derived growth factor, B polypeptide | PDGFB | 1.30 | Binding with adiponectin. Member of the platelet-derived growth factor family. The four members of this family are mitogenic factors for cells of mesenchymal origin. | dermatofibro-sarcoma, meningioma | | RTK (Drosophila melanogaster) | | |

FIG. 2F

| No. | Protein | Gene Name | Fold Increase | Putative/Established Function | Putative/Established Disease Association | Established Adipokine | Receptor | Receptor Location | Comments |
|---|---|---|---|---|---|---|---|---|---|
| 45 | transforming growth factor, beta 2 | TGFβ2 | 1.29 | Member of the TGFB family of cytokines, which are multifunctional peptides that regulate proliferation, differentiation, adhesion, migration, and other functions in many cell types by transducing their signal through combinations of transmembrane type I and type II receptors (TGFβR1 and TGFβR2) and their downstream effectors, the SMAD proteins. | hepatic fibrosis, Diabetes, Alzheimers | | TGFβR1, 2, 3 | ubiquitous | |
| 46 | klotho | KL | 1.28 | One of the factors underlying the degenerative processes (e.g., arteriosclerosis, osteoporosis, and skin atrophy) seen in CRF. Mutations have been associated with aging and bone loss. | CRF, Ageing, Arteriosclerosis | | | | |
| 47 | a disintegrin-like and metallopeptidase (reprolysin type) with thrombospondin type 1 motif. | ADAMTS1 | 1.26 | Inflammation, Anti-tumor growth, anti-angiogenesis. | Bronchial Asthma | | | | |
| 48 | transcobalamin 2 | TCN2 | 1.26 | Cell growth, ion transport, cobalt ion transport, cobalamin metabolic process, cobalamin transport | | | | | |
| 49 | secreted frizzled-related protein 4 | SFRP4 | 1.25 | The expression of SFRP4 in ventricular myocardium correlates with apoptosis related gene expression. Expression increases during adipogenesis. | Cancer, Aging | yes | | | |
| 50 | mannan-binding lectin serine peptidase 1 | MASP1 | 1.22 | Plays an essential role in the innate and adaptive immune response. | Michels syndrome Meningioma | yes | | | |

FIG. 2G

| No. | Protein | Gene Name | Fold Increase | Putative/Established Function | Putative/Established Disease Association | Established Adipokine | Receptor | Receptor Location | Comments |
|---|---|---|---|---|---|---|---|---|---|
| 51 | transmembrane protease, serine 2 | TMPRSS2 | 1.20 | Up-regulated by androgenic hormones in prostate cancer cells and down-regulated in androgen-independent prostate cancer tissue. | | | | | |
| 52 | dystroglycan 1 | DAG1 | 1.16 | In skeletal muscle the dystroglycan complex works as a transmembrane linkage between the extracellular matrix and the cytoskeleton. | Muscular dystrophy | yes | | | |
| 53 | lipoprotein lipase | LPL | 1.11 | Triglyceride hydrolase and ligand/bridging factor for receptor-mediated lipoprotein uptake. | Dyslipidemia, Fatty liver | yes | | | |
| 54 | selenoprotein P, plasma, 1 | SEPP1 | 1.08 | A heparin-binding protein that appears to be associated with endothelial cells, and has been implicated to function as an antioxidant in the extracellular space. Plasma levels of selenoprotein P (SEPP1) have been positively correlated with insulin resistance. | Diabetes, Insulin Resistance, Arteriosclerosis | | | | |

FIG. 3A

Up-Regulated Secreted Proteins from Trained scWAT

| Protein | Gene Name | Fold Increase | Putative/Established Function | Putative/Established Disease Association | Established Adipokine | Receptor | Receptor Location | Comments |
|---|---|---|---|---|---|---|---|---|
| wingless-related MMTV integration site 3 | Wnt3 | 3.82 | Required for primary axis formation in the mouse. May play a role in some cases of human breast, rectal, lung and gastric cancer through activation of the WNT-beta catenin-TCF signaling pathway. Incubation of EMSC adipocytes with Wnt3a for 48 hours increased OCR and mitochondrial genes. | Cancer, Aging | | fz-44 (nematodes) | neuron | Largest increase of secreted proteins and highly significant in mouse. In humans, exercise training increases other WNT family members including 4, 5A, 6, and 7B. Recently, there has been considerable interest in Wnt and Sfpr proteins in adipose biology, especially adipogenesis. |
| brevican | BCAN | 2.19 | Invasion, motility, adhesion, cell growth. | Cancer, Stroke | | | | Increase in human adipose tissue with exercise. In mice, training increases circulating and adipose BCAN protein. |
| paraoxonase 1 | PON1 | 2.18 | Attaches to high density lipoproteins (HDL) particles in serum and plays a crucial role in inhibiting prooxidative damage and LDL oxidation. | CAD, Alzheimers, Diabetes | | | | Training increases family member in human subjects. PON-1 activity inversely correlated with H8A1c. |
| hyaluronan and prot | HAPLN1 | 1.99 | Cell adhesion, skeletal muscle development. | Diabetes, Obesity | | | | Training increases in human adipose tissue. |
| angiopoietin-like 2 | ANGPTL2 | 1.91 | Improves insulin resistance in adipocytes. | Diabetes | yes | | | Recently been shown to improve type 2 diabetes. |
| cysteine-rich secretory protein 1 | CRISP1 | 1.85 | Involved in sperm-egg plasma membrane fusion. | | | | | Has not been studied in adipose tissue but has moderate-high levels of expression. Search of gene array data base shows decreased expression in adipose tissue of obese humans. Training increases CRISP1 mRNA in mice and humans. No working antibody available. |

FIG. 3B

| Protein | Gene Name | Fold Increase | Putative/Established Function | Putative/Established Disease Association | Established Adipokine | Receptor | Receptor Location | Comments |
|---|---|---|---|---|---|---|---|---|
| tissue inhibitor of metalloproteinase 3 | TIMP3 | 1.48 | Anti-TNFa. Involved in apoptosis, growth, invasion, proliferation, malignancy, quantity, cell-cell adhesion, morphology, tubulation, migration. | Cancer | | | | Impaired TIM3 has been linked to development of insulin resistance. |
| transforming growth factor, beta 2 | TGFβ2 | 1.29 | Member of the TGFB family of cytokines, which are multifunctional peptides that regulate proliferation, differentiation, adhesion, migration, and other functions in many cell types by transducing their signal through combinations of transmembrane type I and type II receptors (TGFBR1 and TGFBR2) and their downstream effectors, the SMAD proteins. | hepatic fibrosis, Diabetes, Alzheimers | | TGFβR1, 2, 3 | ubiquitous | Increased with training in both humans and mice. Our muscle studies suggest this signaling pathway is critical for adaptations to exercise training. |
| a disintegrin-like and metallopeptidase (reprolysin type) with thrombospondin type 1 motif, 12 | ADAMTS | 1.26 | Inflammation, Anti-tumor growth, anti-angiogenesis. | Bronchial Asthma | | | | Increased in humans and mice with training. |
| transcobalamin 2 | TCN2 | 1.26 | Cell growth, ion transport, cobalt ion transport. cobalamin metabolic process, cobalamin transport | | | | | Increased in humans and mice with training. |

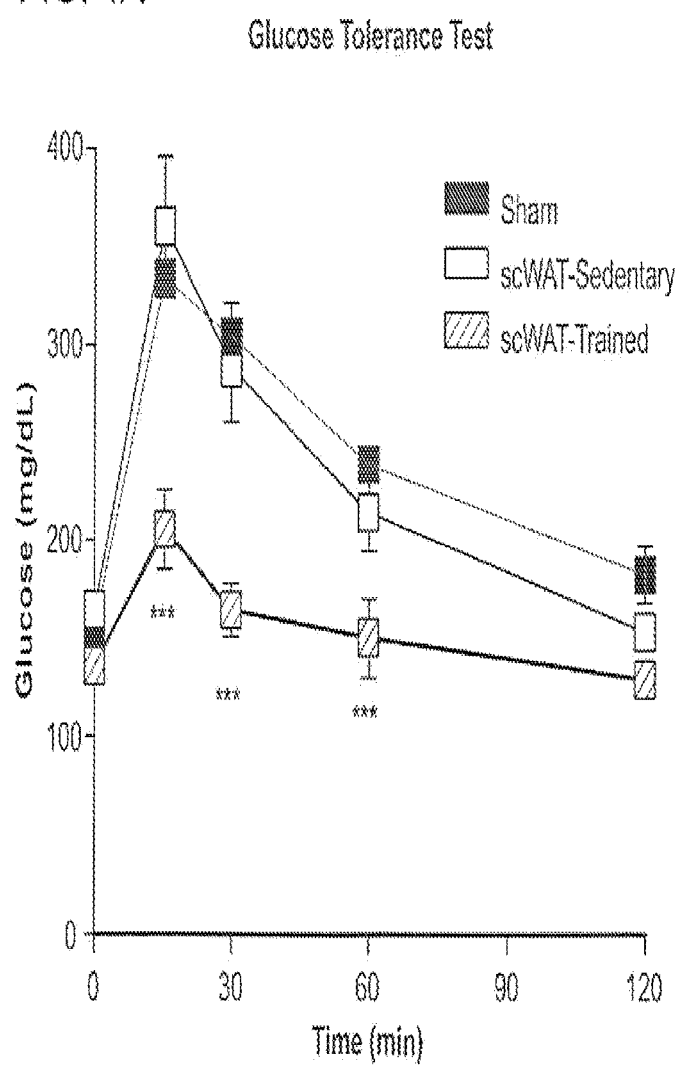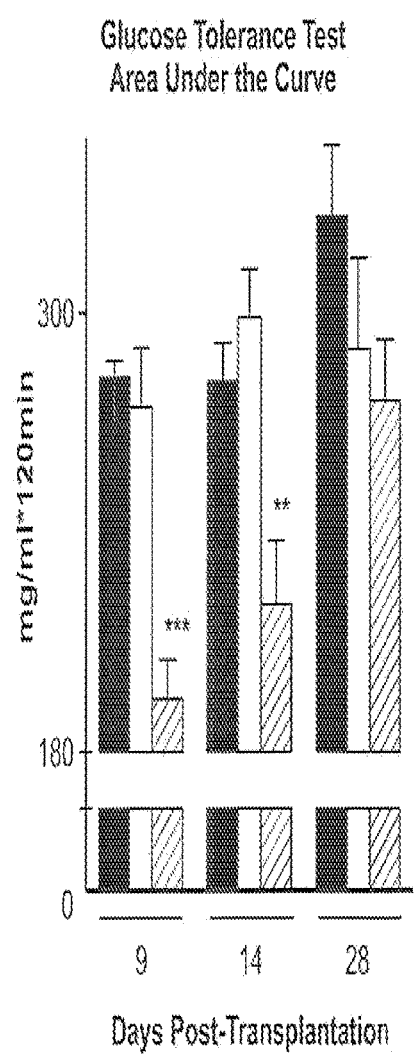

FIG. 6 Glucose Uptake in Isolated Mouse Soleus Muscles
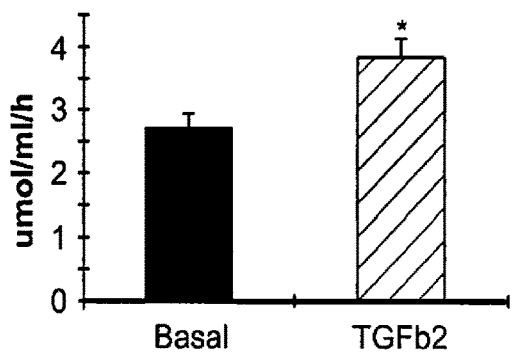
FIG. 7 Effects of WNT3a on Glucose Uptake
C2C12 muscle cells
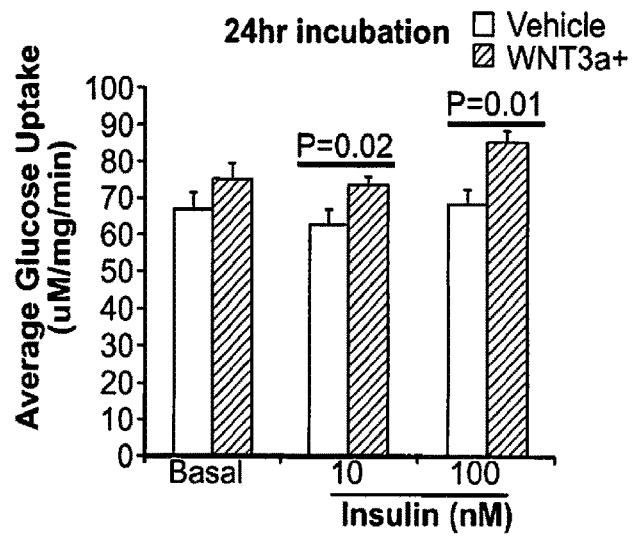
FIG. 8 Effects of WNT3a on Glucose Uptake
3T3L1 adipose cells
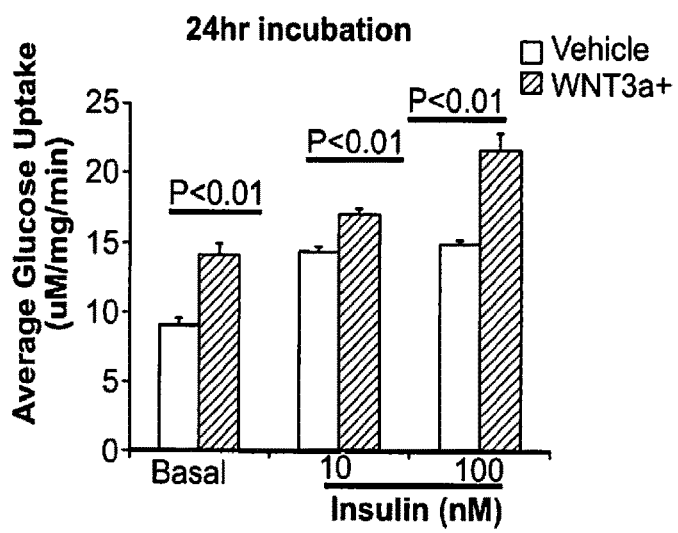

US 10,632,175 B2

EXERCISE-REGULATED ADIPOKINES AS THERAPY FOR DIABETES MANAGEMENT

This work was supported by grant R21 DK091764 from the National Institutes of Health (NIH) and the National Institute of Diabetes and Digestive and Kidney Diseases (NIDDK). The government may have certain rights to the invention.

BACKGROUND OF THE INVENTION

The identification of factors effective in modulating diabetes and glucose metabolism in subjects needing such intervention such as, for example, persons with diabetes (type I or type II) is needed. Persons suffering from defects in glucose metabolism and diabetes have limited treatment options at the present time. Current research is focused on the identification and synthesis of, for example, small molecules suitable for intervention. Exercise is known to modulate glucose metabolism and have modulating effects on diabetes in patient subjects. [Kourtoglou, Diabetes. Res. Clin. Pract. 93 Suppl 1:S73-7 (2011); Brandt and Pedersen, J. Biomed. Biotechnol. 2010: 520258-64 (2010); Goodyear and Kahn, Ann. Rev. Med. 49: 235-261 (1998); Sigel et al., Diabetes Care 27: 2518-39 (2004)]. Still, little work has been directed towards the physiological basis for these observations. What is needed are methods for the identification of native physiological pathways and factors that mediate glucose control and metabolism in vivo.

SUMMARY OF THE INVENTION

An emerging concept in metabolic research is that physical exercise activates tissue-to-tissue communication throughout the organism and this tissue "cross-talk" can mediate some of the beneficial metabolic effects of exercise. Investigation of exercise-induced tissue cross-talk has been focused on muscle-derived myokines that may function in both an autocrine and endocrine fashion. More recently, a novel concept and approach developed by the present Inventors in exercise biology is that exercise training regulates adipose tissue in a manner that results in tissue-to-tissue communication between adipose tissue and skeletal muscle, liver, heart, brown adipose tissue, and potentially many other tissues. The present invention provides methods of identifying the factors that mediate cross-talk between adipose tissue and other tissues that are effective in the modulation of glucose control, glycemic control and metabolism and modulation of diabetes (esp., type II diabetes) in subjects. Further, the present invention is related to methods and compositions effective in regulating glucose tolerance (glycemic control) in subject individuals in need of the regulation of glucose tolerance. Also, the present invention relates to control of or modulation of insulin sensitivity, glucose control, weight loss, lipid control and cardiovascular control in individuals in need of said control and/or modulation. Said individuals may have diabetes or be prediabetic.

BRIEF DESCRIPTION OF THE FIGURES

FIG. 2 shows a chart listing secreted proteins that have been identified in the present invention as prospective adipokines.

FIG. 3 shows a chart listing the most effective adipokines as disclosed in FIG. 2.

One of the putative adipokines identified is TGFβ2.

FIG. 6 shows effect of incubating intact soleus muscles with TGFβ2 for 4 hrs. This incubation significantly increased glucose uptake, showing physiological relevance.

Figure 1:
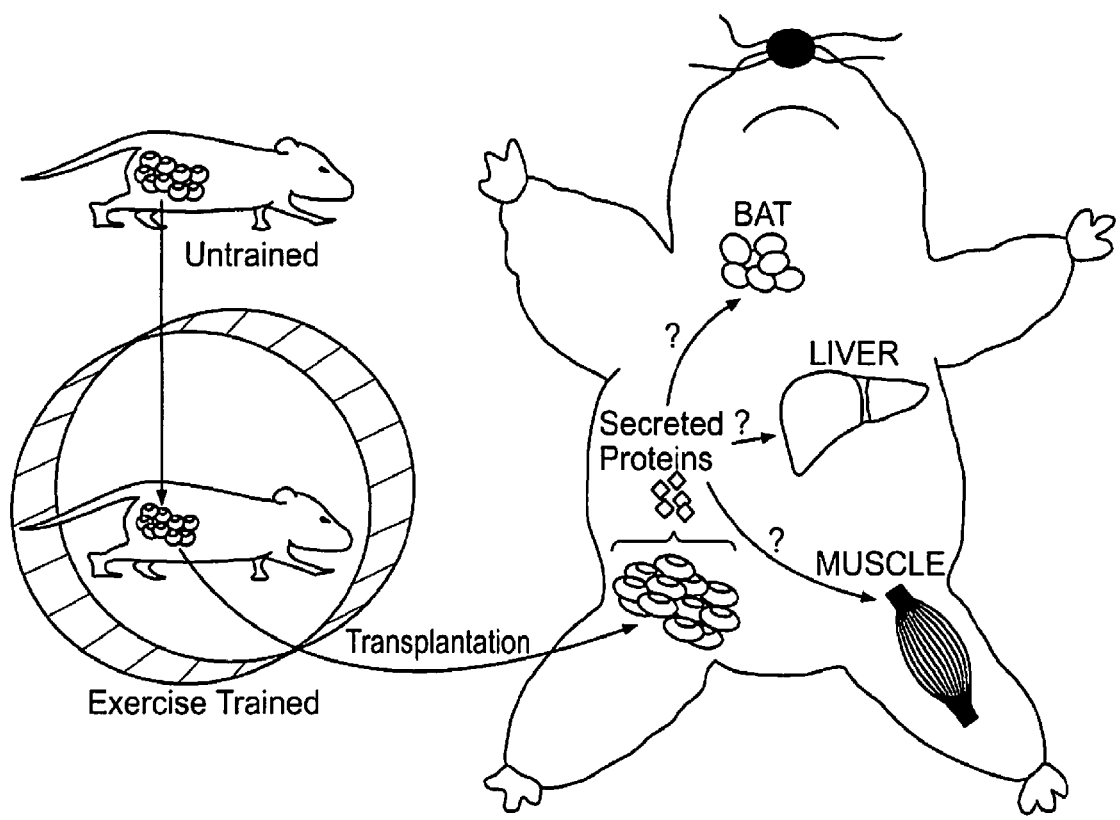
FIG. 1 shows a proposed model for the effects of exercise-trained subcutaneous adipose tissue on glucose homeostasis. Data show that exercise training results in profound adaptations to subcutaneous white adipose tissue. It also shows that transplantation of exercise-trained subcutaneous adipose tissue into a sedentary recipient mouse improves glucose homeostasis. This effect is mediated by secreting proteins called "adipokines" that have endocrine effects to increase metabolism in multiple tissues including skeletal muscle, liver and brown adipose tissue (BAT).

Another identified adipokines is Wnt3a.

FIG. 7 shows that incubation of C2C12 muscle cells with Wnt3a increases glucose uptake.

FIG. 8 shows that incubation of 3T3L1 adipose cells with Wnt3a increases glucose uptake.

DETAILED DESCRIPTION OF THE PRESENT INVENTION

The present invention relates to methods and compositions use for the treatment of subjects in need of Glycemic control, glucose tolerance and glucose homeostasis. Cross-talk between various cells and even differing tissue types is becoming understood as instrumental the regulation of homeostasis, the breakdown or disregulation of which may be causative in various disease states. The present invention is related to the discovery of factors produced by adipose tissue that are stimulated by exercise. In this regard, exercise induces adipose tissues to produce a range of proteins. The majority of these proteins, before the present discovery, were not known to be related to adipose tissues, nor known to be involved in the regulation of glucose (glycemic control, glucose homeostasis) in subjects. None were known to be stimulated in adipose tissues by exercise. These discoveries are based, at least in part, on experiments wherein the transplantation of subcutaneous white adipose tissue from exercise-trained mice into the visceral cavity of recipient sedentary mice significantly improved glucose tolerance compared to transplantation of subcutaneous white adipose tissue from sedentary mice. Mice transplanted with subcutaneous white adipose tissue from trained donors also had a significant increase in glucose disposal into skeletal muscle and brown adipose tissue, lower circulating insulin, glucose, and lipid levels, as well as complete protection from the deleterious effects of high fat feeding.

"Glucose tolerance" is the ability of a subject to regulate blood glucose levels to normal, accepted ranges, i.e., to maintain glucose homeostasis or control blood glucose levels. A glucose tolerance test is a test in which glucose is given to a subject and the rate of clearance from the blood is measured.

"Impaired glucose tolerance" (IGT) is a pre-diabetic state of hyperglycemia that is associated with insulin resistance and increased risk of cardiovascular pathology. IGT may precede type 2 diabetes mellitus by many years. IGT is also a risk factor for mortality.

"Lipid control" in defined herein as the regulation of lipids in a subject. Lipid control in often not adequately regulated in a subject due to medical conditions such as diabetes thereby causing, for example, weight gain. Thus, the present invention can aid subjects in "lipid management" by modulating lipid control.

"Cardiovascular control" is defined herein as modulating conditions that may lead to cardiovascular disease and/or pre-cardiovascular disease, such as angina, blood clots and other conditions brought about by glucose and lipid imbalance in a subject. Thus, the present invention can aid subjects in managing cardiovascular disease conditions and pre-disease conditions by modulating glucose and lipid management in the subject.

Measuring Glycemic Control and Glucose Tolerance in a Subject

The term "Glycemic control" and methods of monitoring glycemic control (and, by extension, glucose tolerance) are known to those of ordinary skill in the art.

"Glycemic control" is a medical term referring to the typical levels of blood sugar (glucose) in a person with diabetes mellitus. Much evidence suggests that many of the long-term complications of diabetes, especially the microvascular complications, result from many years of hyperglycemia (elevated levels of glucose in the blood). Good glycemic control, in the sense of a "target" for treatment, has become an important goal of diabetes care, although recent research suggests that the complications of diabetes may be caused by genetic factors or, in type 1 diabetics, by the continuing effects of the autoimmune disease which first caused the pancreas to lose its insulin-producing ability.

Because blood sugar levels fluctuate throughout the day and glucose records are imperfect indicators of these changes, the percentage of hemoglobin which is glycosylated is used as a proxy measure of long-term glycemic control in research trials and clinical care of people with diabetes. This test, the hemoglobin A1c or glycosylated hemoglobin reflects average glucoses over the preceding 2-3 months. In nondiabetic persons with normal glucose metabolism the glycosylated hemoglobin is usually 4-6% by the most common methods (normal ranges may vary by method).

"Perfect glycemic control" would mean that glucose levels were always normal (70-130 mg/dl, or 3.9-7.2 mmol/L) and indistinguishable from a person without diabetes. In reality, because of the imperfections of treatment measures, even "good glycemic control" describes blood glucose levels that average somewhat higher than normal much of the time. In addition, one survey of type 2 diabetics found that they rated the harm to their quality of life from intensive interventions to control their blood sugar to be just as severe as the harm resulting from intermediate levels of diabetic complications.

Accepted "target levels" of glucose and glycosylated hemoglobin that are considered good control have been lowered over the last 25 years, because of improvements in the tools of diabetes care, because of increasing evidence of the value of glycemic control in avoiding complications, and by the expectations of both patients and physicians. What is considered "good control" also varies by age and susceptibility of the patient to hypoglycemia.

In the 1990s the American Diabetes Association (ADA) conducted a publicity campaign to persuade patients and physicians to strive for average glucose and hemoglobin A1c values below 200 mg/dl (11 mmol/l) and 8%. Currently many patients and physicians attempt to do better than that.

Poor glycemic control refers to persistently elevated blood glucose and glycosylated hemoglobin levels, which may range from 200-500 mg/dl (11-28 mmol/L) and 9-15% or higher over months and years before severe complications occur.

Personal (Home) Glucose Monitoring

Control and outcomes of both types 1 and 2 diabetes may be improved by patients using home glucose meters to regularly measure their glucose levels. Glucose monitoring is both expensive (largely due to the cost of the consumable test strips) and requires significant commitment on the part of the patient. The effort and expense may be worthwhile for patients when they use the values to sensibly adjust food, exercise, and oral medications or insulin. These adjustments are generally made by the patients themselves following training by a clinician.

Regular blood testing, especially in type 1 diabetics, is helpful to keep adequate control of glucose levels and to reduce the chance of long term side effects of the disease. There are many (at least 20+) different types of blood monitoring devices available on the market today. The principle of the devices is virtually the same: a small blood sample is collected and measured. In one type of meter, the electrochemical, a small blood sample is produced by the patient using a lancet (a sterile pointed needle). The blood droplet is usually collected at the bottom of a test strip, while the other end is inserted in the glucose meter. This test strip contains various chemicals so that when the blood is applied, a small electrical charge is created between two contacts. This charge will vary depending on the glucose levels within the blood. In older glucose meters, the drop of blood is placed on top of a strip. A chemical reaction occurs and the strip changes color. The meter then measures the color of the strip optically.

Self-testing is clearly important in type I diabetes where the use of insulin therapy risks episodes of hypoglycemia and home-testing allows for adjustment of dosage on each administration. However its benefit in type 2 diabetes is more controversial as there is much more variation in severity of type 2 cases. It has been suggested that some type 2 patients might do as well with home urine-testing alone. The best use of home blood-sugar monitoring is being researched.

Continuous Glucose Monitoring (CGM) CGM technology has been rapidly developing to give people living with diabetes an idea about the speed and direction of their glucose changes. While it still requires calibration from SMBG and is not indicated for use in correction boluses, the accuracy of these monitors are increasing with every innovation.

HbA1c Test

A useful test that has usually been done in a laboratory is the measurement of blood HbA1c levels. This is the ratio of glycated hemoglobin in relation to the total hemoglobin. Persistent raised plasma glucose levels cause the proportion of these molecules to go up. This is a test that measures the average amount of diabetic control over a period originally thought to be about 3 months (the average red blood cell lifetime), but more recently thought to be more strongly weighted to the most recent 2 to 4 weeks. In the non-diabetic, the HbA1c level ranges from 4.0-6.0%; patients with diabetes mellitus who manage to keep their HbA1c level below 6.5% are considered to have good glycemic control. The HbA1c test is not appropriate if there has been changes to diet or treatment within shorter time periods than 6 weeks or there is disturbance of red cell aging (e.g. recent bleeding or hemolytic anemia) or a hemoglobinopathy (e.g., sickle cell disease). In such cases the alternative Fructosamine test is used to indicate average control in the preceding 2 to 3 weeks.

Ongoing Monitoring

Recently, devices have been manufactured which provide ongoing monitoring of glucose levels on an automated basis during the day, for example:

1. The Minimed Paradigm REAL-Time by Minimed, is a continuous glucose monitoring system (CGMS) that provides blood glucose measurements to be made every five minutes over a three-day period. The patient can thus adjust an insulin infusion pump immediately and mimic the "feed-back" mechanism of a pancreas.
2. The Dexcom Seven™ by Dexcom, is another blood glucose monitoring device. Like the Minimeds Paradigm, it provides measurement every 5 minutes. The sensors lasts 7 days (against medtronics 3 day sensor) before they have to be changed.
3. The US Food and Drug Administration (FDA) has also approved a non-invasive blood glucose monitoring device, the GlucoWatch G2 Biographer (Cygnus, Inc., Redwood City, Calif.). This allows checking blood glucose levels, while puncturing the skin as little as twice a day. Once calibrated with a blood sample, it pulls body fluids from the skin using small electrical currents, taking six readings an hour for as long as thirteen hours. It has not proven to be reliable enough, or convenient enough to be used in lieu of conventional blood monitoring. Other non-invasive methods like radio waves, ultrasound and energy waves are also being tested. The accuracies of these non-invasive devices are at the current stage behind the devices that are inserted or operated into the body.
4. In the fall of 2010 FDA tightened the document requirements needed for receiving FDA approval for CGMS devices and insulin-pump/CGMS devices. As a result, release dates of many innovative and improved systems are delayed until 2012 and later.

Pharmaceutical Compositions

The methods described herein include the manufacture and use of pharmaceutical compositions, which include compounds identified by a method described herein as active ingredients. Also included are the pharmaceutical compositions themselves.

The factors identified by the present invention will, in some circumstances, be formulated into pharmaceutical compositions. Pharmaceutical compositions typically include a pharmaceutically acceptable carrier. As used herein the language "pharmacological composition," "pharmacological carrier" or "pharmaceutically acceptable carrier" includes compositions and carriers comprising one or more of, for example, saline, solvents, dispersion media, coatings, antibacterial and antifungal agents, isotonic and absorption delaying agents, buffers and the like, compatible with pharmaceutical administration. Supplementary active compounds can also be incorporated into the compositions. Suitable pharmaceutical compositions and carriers are also defined herein to include compositions and carriers suitable for in vitro use, e.g., for diagnostic use, research use and ex vivo manipulation of cells and tissues.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known to one of ordinary skill in the art, see, e.g., the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use can include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile or capable of being sterilized and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL® (sodium starch glycollate), or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798, which is incorporated herein by reference.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art, or into adhesive pads, as is generally known in the art.

The pharmaceutical compositions can also be prepared in the form of suppositories (e.g., with conventional suppository bases such as cocoa butter and other glycerides) or retention enemas for rectal delivery.

The therapeutic compounds may include proteins of one or more of the factors identified herein or functional or structural analogs thereof, or mutants thereof. Any biologically functional fragment, functional analog, structural analog or mutants of the factors (i.e., the proteins) identified in FIGS. 2 and 3 of the present specification are contemplated to be effective in the methods of the present invention. One of ordinary skill in the art can produce and test the effective levels of such fragments, analogs and mutants based on the teachings of the present invention. Further, such fragments, analogs or mutants may be synthetic or naturally occurring. Further still, the sequences of the proteins given in FIGS. 2 and 3 (and analogs and homologs thereof) are know to one of ordinary skill in the art as exemplified by the sequence listings in available data banks such as GenBank.

Therapeutic compounds may include nucleic acids (i.e., a nucleic acid encoding one or more of the factors identified herein or functional or structural analogs thereof) can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587, which are incorporated herein by reference. Additionally, intranasal delivery is possible, as described in, inter alia, Hamajima, et al., Clin. Immunol. Immunopathol. 88(2), 205-10 (1998). Liposomes (e.g., as described in U.S. Pat. No. 6,472,375, which is incorporated herein by reference) and microencapsulation can also be used. Biodegradable targetable microparticle delivery systems can also be used (e.g., as described in U.S. Pat. No. 6,471,996, which is incorporated herein by reference).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques as are known to one of ordinary skill in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, which is incorporated herein by reference.

The pharmaceutical compositions can be included in a kit, container, pack or dispenser together with instructions for administration.

Methods of Treatment

The methods described herein include methods for the treatment of disorders associated with impaired glucose tolerance, e.g., for the improvement of glycemic control, insulin sensitivity, weight loss, lipid control and cardiovascular control. In some embodiments, the disorder is type 1 or type 2 diabetes. Generally, the methods include administering a therapeutically effective amount of therapeutic compound as described herein, to a subject who is in need of, or who has been determined to be in need of, such treatment.

As used in this context, to "treat" means to ameliorate at least one symptom of the disorder associated with impaired glucose tolerance. Often, impaired glucose tolerance results in hyperglycemia; thus, a treatment can result in a return or approach to normoglycemia/normal insulin sensitivity. As used in this context, to "prevent diabetes," "prevent type 1 diabetes" or "prevent type 2 DM" (i.e., type 2 diabetes mellitus), or similar, means to reduce the likelihood that a subject will develop diabetes, type 1 diabetes or type 2 DM, respectively. One of skill in the art will appreciate that a preventive treatment is not required to be 100% effective, but can instead result in a delay in the onset of T1D, T2DM, or a reduction in symptoms, e.g., an improvement in glucose tolerance.

Dosage, toxicity and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

An "effective amount," "therapeutic amount" or "sufficient amount" is an amount sufficient to effect beneficial or desired results. For example, a therapeutic amount is one that achieves the desired therapeutic effect. This amount can be the same or different from a prophylacticly effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments. The terms "administer," "administered," administering," etc., also includes the terms "caused to be administered" and "causing to be administered," etc., by, for example, giving instruction to another to administer.

The pharmaceutical compositions can be included in a container, pack, or dispenser together with instructions for administration.

In some embodiments, the pharmaceutical composition is injected into a tissue, e.g., adipose tissue, muscle tissue or liver tissue.

Gene Therapy

The nucleic acids described, referenced or otherwise indicated herein (for example, a nucleic acid encoding one or more of the proteins listed in FIGS. 2 and 3, the sequences of which can be found by one of ordinary skill in the art at, e.g., GenBank) can be incorporated into a gene construct to be used as a part of a gene therapy protocol to deliver nucleic acids encoding either an agonistic or antagonistic form of an factor or agent described herein or an active fragment thereof or a functional or structural analog thereof. The invention features expression vectors for in vivo transfection and expression of one or more of the proteins listed in FIGS. 2 and 3 or an active fragment thereof or a functional or structural analog thereof, described herein. Expression constructs of such components may be administered in any biologically effective carrier, e.g., any formulation or composition capable of effectively delivering the component gene to cells in vivo, as are known to one of ordinary skill in the art. Approaches include insertion of the subject gene in viral vectors including recombinant retroviruses, adenovirus, adeno-associated virus and herpes simplex virus-1, or recombinant bacterial or eukaryotic plasmids. Viral vectors transfect cells directly; plasmid DNA can be delivered with the help of, for example, cationic liposomes (e.g., LIPOFECTIN™) or derivatized (e.g., antibody conjugated), polylysine conjugates, gramicidin S, artificial viral envelopes or other such intracellular carriers, as well as direct injection of the gene construct or $CaPO_4$ precipitation carried out in vivo, as is known to one of ordinary skill in the art.

One approach for in vivo introduction of nucleic acid into a cell is by use of a viral vector containing nucleic acid, e.g., a cDNA, encoding an alternative pathway component described herein. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see, e.g., Miller, Blood 76:271-78 (1990)). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, et al., (eds.) Greene Publishing Associates, (1989), Sections 9.10-9.14, and other standard laboratory manuals. Non-limiting examples of suitable retroviruses include pLJ, pZIP, pWE and pEM which are known to those of ordinary skill in the art. Examples of suitable packaging virus lines for preparing both ecotropic and amphotropic retroviral systems include *Crip, *Cre, *2 and *Am. Retroviruses have been used to introduce a variety of genes into many different cell types, including epithelial cells, in vitro and/or in vivo (see, for example, Eglitis, et al., Science 230:1395-1398 (1985); Danos and Mulligan, Proc. Natl. Acad. Sci. USA 85:6460-6464 (1988); Wilson, et al., Proc. Natl. Acad. Sci. USA 85:3014-3018 (1988); Armentano, et al., Proc. Natl. Acad. Sci. USA 87:6141-6145 (1990); Huber, et al., Proc. Natl. Acad. Sci. USA 88:8039-8043 (1991); Ferry, et al., Proc. Natl. Acad. Sci. USA 88:8377-8381 (1991); Chowdhury, et al., Science 254:1802-1805 (1991); van Beusechem, et al., Proc. Natl. Acad. Sci. USA 89:7640-7644 (1992); Kay, et al., Human Gene Therapy 3:641-647 (1992); Dai, et al., Proc. Natl. Acad. Sci. USA 89:10892-10895 (1992); Hwu, et al., J. Immunol. 150:4104-4115 (1993); U.S. Pat. Nos. 4,868,116; 4,980,286; PCT Application WO 89/07136; PCT Application WO 89/02468; PCT Application WO 89/05345; and PCT Application WO 92/07573; all of which are incorporated herein by reference in their entirety).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner, et al., BioTechniques 6:616 (1988); Rosenfeld, et al., Science 252:431-434 (1991); and Rosenfeld, et al., Cell 68:143-155 (1992). Suitable adenoviral vectors derived from the adenovirus strain Ad type 5 d1324 or other strains of adenovirus (e.g., Ad2, Ad3, Ad7 etc.) are known to those of ordinary skill in the art. Recombinant adenoviruses can be advantageous in certain circumstances in that they are not capable of infecting non-dividing cells and can be used to infect a wide variety of cell types, including epithelial cells (Rosenfeld, et al. (1992), supra). Furthermore, the virus particle is relatively stable and amenable to purification and concentration and, as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner, et al. (1998), supra; Haj-Ahmand and Graham, J. Virol. 57:267 (1986)).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka, et al., Curr. Topics in Micro. and Immunol. 158:97-129 (1992)). It is also one of the few viruses that may integrate its DNA into non-dividing cells, and exhibits a high frequency of stable integration (see for example Flotte, et al., Am. J. Respir. Cell. Mol. Biol. 7:349-356 (1992); Samulski, et al., J. Virol. 63:3822-3828 (1989); and McLaughlin, et al., J. Virol. 62:1963-1973 (1989)). Vectors containing as little as 300 base pairs of AAV can be packaged and can integrate. Space for exogenous DNA is limited to about 4.5 kb. An AAV vector such as that described in Tratschin, et al., Mol. Cell. Biol. 5:3251-3260 (1985) can be used to introduce DNA into cells. A variety of nucleic acids have been introduced into different cell types using AAV vectors (see for example Hermonat, et al., Proc. Natl. Acad. Sci. USA 81:6466-6470 (1984); Tratschin, et al., Mol. Cell. Biol. 4:2072-2081 (1985); Wondisford, et al., Mol. Endocrinol. 2:32-39 (1988); Tratschin, et al., J. Virol. 51:611-619 (1984); and Flotte, et al., J. Biol. Chem. 268:3781-3790 (1993)).

In addition to viral transfer methods, such as those illustrated above, non-viral methods can also be employed to cause expression of an nucleic acid agent encoding one or more of the proteins listed in FIGS. 2 and 3 or an active fragment thereof or a functional or structural analog thereof polypeptide encoding nucleic acid) in the tissue of a subject. Most nonviral methods of gene transfer rely on normal mechanisms used by mammalian cells for the uptake and intracellular transport of macromolecules. In some embodiments, non-viral gene delivery systems of the present invention rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli, et al., J. Invest. Dermatol. 116 (1):131-135 (2001); Cohen, et al., Gene Ther 7 (22):1896-905 (2000); or Tam, et al., Gene Ther. 7 (21):1867-74 (2000).

In a representative embodiment, a gene encoding a peptide identified herein can be entrapped in liposomes bearing positive charges on their surface (e.g., lipofectins) and (optionally) which are tagged with antibodies against cell surface antigens of the target tissue (Mizuno, et al., No Shinkei Geka 20:547-551 (1992); PCT publication WO91/06309; Japanese patent application 1047381; and European patent publication EP-A-43075).

In clinical settings, the gene delivery systems for the therapeutic gene can be introduced into a patient by any of a number of methods, each of which is familiar in the art. For instance, a pharmaceutical preparation of the gene delivery system can be introduced systemically, e.g., by intravenous injection. Specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see, U.S. Pat. No. 5,328,470) or by stereotactic injection (e.g., Chen, et al., PNAS 91: 3054-3057 (1994)).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g., retroviral vectors, the pharmaceutical preparation can comprise one or more cells which produce the gene delivery system.

Cell Therapy

An agent described herein suitable for, for example, improving glycemic control, e.g., a one or more of the proteins identified in FIGS. 2 and 3 (the sequences of which can be found by one of ordinary skill in the art at, for example, GenBank) or an active fragment thereof or a functional or structural analog thereof, can also be increased in a subject by introducing into a cell, e.g., a muscle cell, liver cell or adipose cell. The nucleotide sequence can include a promoter sequence, e.g., a promoter sequence from the gene encoding the identified protein or from another gene; an enhancer sequence, e.g., 5' untranslated region (UTR), e.g., a 5' UTR, a 3' UTR; a polyadenylation site; an insulator sequence; or another sequence that modulates the expression of the gene, or an active fragment thereof or a functional or structural analog thereof. The cell can then be introduced into the subject by methods know to one of ordinary skill in the art.

Primary and secondary cells to be genetically engineered can be obtained from a variety of tissues and include cell types which can be maintained and propagated in culture. For example, primary and secondary cells include adipose cells, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells (myoblasts) and precursors of these somatic cell types. Primary cells are preferably obtained from the individual to whom the genetically engineered primary or secondary cells are administered. However, primary cells may be obtained for a donor (other than the recipient). The preferred cell for the compositions and methods of the present invention is an adipose cell(s), a liver cell(s) or muscle cell(s).

The term "primary cell" includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. Secondary cells are cell strains which consist of secondary cells which have been passaged one or more times.

Primary or secondary cells of vertebrate, particularly mammalian, origin can be transfected with an exogenous nucleic acid sequence which includes a nucleic acid sequence encoding a signal peptide, and/or a heterologous nucleic acid sequence (e.g., encoding one or more of the factors identified in FIGS. 2 and 3, or an active fragment thereof or a functional or structural analog thereof) and produce the encoded product stably and reproducibly in vitro and in vivo, over extended periods of time (i.e., hours, days, weeks or longer). A heterologous amino acid can also be a regulatory sequence, e.g., a promoter, which causes expression, e.g., inducible expression or upregulation, of an endogenous sequence. An exogenous nucleic acid sequence can be introduced into a primary or secondary cell by homologous recombination as described, for example, in U.S. Pat. No. 5,641,670, the contents of which are incorporated herein by reference. The transfected primary or secondary cells may also include DNA encoding a selectable marker which confers a selectable phenotype upon them, facilitating their identification and isolation.

Vertebrate tissue can be obtained by standard methods such a punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell including calcium phosphate or calcium chloride precipitation, microinjection, DEAE-dextrin-mediated transfection, lipofection or electroporation, all of which are routine in the art.

Transfected primary or secondary cells undergo sufficient number doubling to produce either a clonal cell strain or a heterogeneous cell strain of sufficient size to provide the therapeutic protein to an individual in effective amounts. The number of required cells in a transfected clonal heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient.

The transfected cells, e.g., cells produced as described herein, can be introduced into an individual to whom the product is to be delivered. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used. Preferred sites for introduction are the pancreas or the liver. Once implanted in individual, the transfected cells produce the product encoded by the heterologous DNA or are affected by the heterologous DNA itself. For example, an individual who suffers from disease related to impaired glycemic control is a candidate for implantation of cells producing an agent or factor described herein (see, FIGS. 2 and 3) or an active fragment thereof or a functional or structural analog or mimic thereof as described herein or known to those of ordinary skill in the art.

An immunosuppressive agent, e.g., drug, or antibody, can be administered to a subject at a dosage sufficient to achieve the desired therapeutic effect (e.g., inhibition of rejection of the cells). Dosage ranges for immunosuppressive drugs are known in the art. See, e.g., Freed, et al., N. Engl. J. Med. 327:1549 (1992); Spencer, et al., N. Engl. J. Med. 327:1541 (1992); Widner, et al., N. Engl. J. Med. 327:1556 (1992)). Dosage values may vary according to factors such as the disease state, age, sex, and weight of the individual.

All references cited herein are incorporated herein by reference in their entirety and are representative of what one of ordinary skill in the art knew at the time of the present invention.

EXEMPLIFICATION

Example 1

Fat Transplantation

We have generated considerable preliminary data in support of the hypothesis that exercise training causes adaptations to scWAT that result in secretion of adipokines that in turn function in an endocrine manner to improve whole-body and tissue glucose homeostasis. Remarkably, transplantation of subcutaneous white adipose tissue from exercise-trained mice into the visceral cavity of recipient sedentary mice significantly improved glucose tolerance compared to transplantation of subcutaneous white adipose tissue from sedentary mice. Mice transplanted with subcutaneous white adipose tissue from trained donors also had a significant increase in glucose disposal into skeletal muscle and brown adipose tissue, lower circulating insulin, glucose, and lipid levels, as well as protection from the deleterious effects of high fat feeding. See, FIG. 1 for a schematic diagram of the model proposed based on the present invention.

Transplantation of scWAT from Exercise-Trained Mice Improves Glucose Homeostasis.

To begin to test the novel hypothesis that adipose tissue from trained mice exerts metabolic effects on glucose homeostasis, we have used a transplantation model. Male mice (12 wk old) were given free access to a training wheel (Trained) or were housed individually in standard cages (Sedentary) for 11 days. This duration of training provided a significant training stimulus without a substantial loss of adipose tissue, which can occur with longer periods of training. Trained mice completed a total of 70±8 km during the 11 days.

The procedure was performed as follows. Twelve-week-old male C57BL/6 mice (Charles River Laboratories) were used as both donor and recipient mice for transplantation studies. Fat transplantation was performed using white adipose tissue removed from the subcutaneous (retroperitoneal) and intra-abdominal perigonadal (visceral) areas of trained and sedentary mice. Donor mice were sacrificed by cervical dislocation and fat pads were removed and kept in saline in a 37° C. water bath until transplantation. Recipient mice were anesthetized by intraperitoneal injection of 85-100 mg/kg body weight of pentobarbital. For each recipient mouse, 0.85 g of scWAT or 1.0 g of visceral adipose tissue was transplanted into the visceral cavity. The tissue was carefully lodged deep between folds within sliced portions of endogenous perigonadal adipose tissue of the recipient and lodged next to the mesenteric adipose tissue just below the liver (Tran T T, Yamamoto Y, Gesta S, Kahn C R. Beneficial effects of subcutaneous fat transplantation on metabolism. Cell Metab. 2008; 7(5):410-420; which exemplifies what is known by one of ordinary skill in the art with regard to murine fat transplantation). Adipose tissue from approximately 4 trained mice and 2 sedentary mice was used in order to equalize the amount of transplanted adipose tissue. Sham treated "recipient" mice underwent the same surgical procedure, but no adipose tissue was transplanted. All recipient mice were sedentary throughout the study (i.e., housed in static cages). There appeared to be no difference in rate of recovery after the surgery among the groups based on similar body weights and close monitoring of mice for several days post-transplant.

Figure 4D:
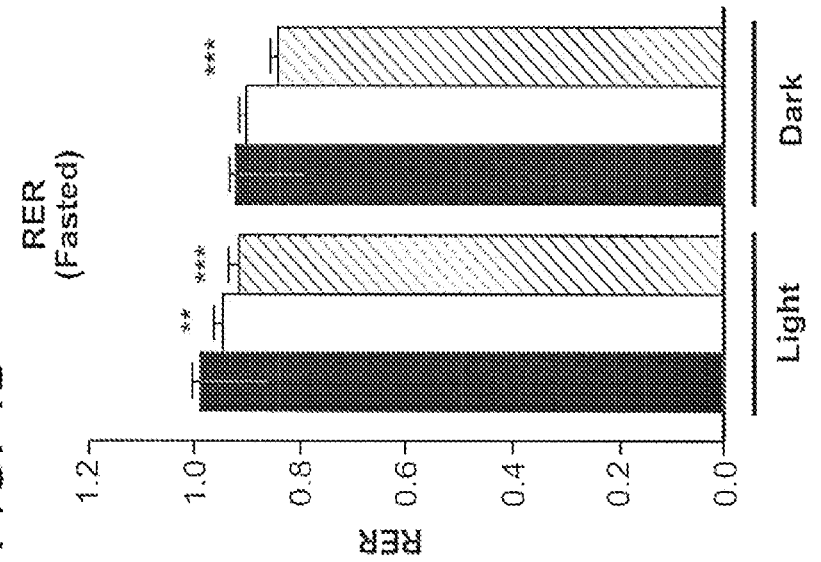
FIG. 4 shows transplantation of trained scWAT into sedentary recipients improves glucose homeostasis. Mice (12 wk old) were transplanted with 0.85 g scWAT (scWAT) from Trained (Red) or Sedentary (Sed) (White) mice, or were sham-operated (Black). (A) Glucose tolerance test (GTT; 2 g glucose/kg, i.p.) at 9 days post-transplantation, (B) Calculated area under the curve (AUC) from GTTs at 9, 14, and 28 days post-transplantation, (C) Homeostasis model of assessment-insulin resistance (HOMA-IR) at 9 days post-transplantation and (D) Respiratory exchange ratio (RER). N=7/group, p<0.01; *p<0.001 compared to sham-operated mice.

For transplantation, trained and sedentary mice were anesthetized and visceral (1.0 g) and subcutaneous (0.85 g) white adipose tissues were removed and implanted into the visceral cavity of a separate cohort of recipient mice (41). In order to transplant equal amounts of adipose tissue, adipose tissue from approximately 2 sedentary mice and 4 trained mice was used. Sham-treated "recipient" mice underwent the same surgical procedure, but no adipose tissue was transplanted. Recipient mice were closely monitored after transplantation, and there were no differences in recovery among the three groups as indicated by normal stature, similar body weights post-transplantation, and no elevation in plasma markers of inflammation or fever (TNF-α, IL-6). Dissection of mice nine days post-transplant revealed the presence of the transplanted tissue and histology showed intact adipocytes and vascularization (data not shown). All recipient mice were sedentary throughout the protocol. Initial assessment of glucose homeostasis was measured by glucose tolerance tests. Nine days post-transplantation, there was a dramatic improvement in glucose tolerance in mice receiving scWAT from exercise-trained mice compared to both mice receiving scWAT from sedentary mice and sham controls (FIG. 4A). In fact, the calculated glucose area under the curve (AUC) for the mice transplanted with trained scWAT was only 66% of the sham controls (FIG. 4B). These intriguing data were the first to suggest that scWAT from exercise-trained mice can exert beneficial effects on glucose tolerance.

Figure 4C:
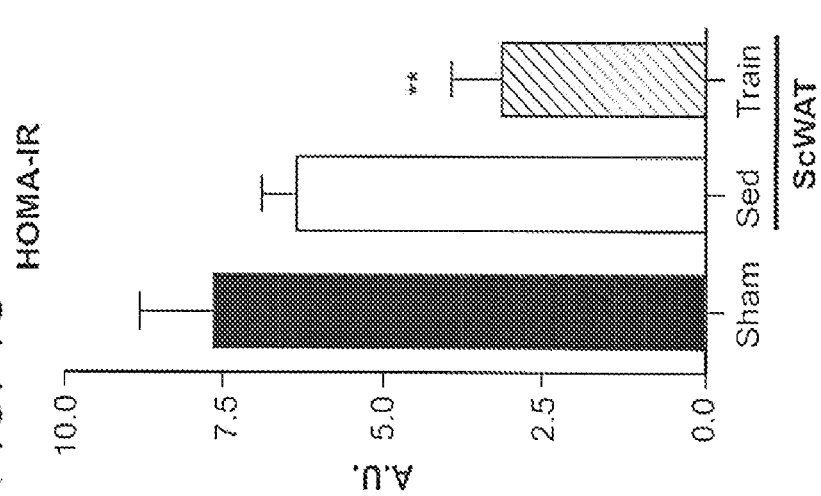

In addition to the marked improvement in glucose tolerance, mice transplanted with trained scWAT exhibited a significant decrease in fasting blood glucose, insulin, and cholesterol concentrations nine days post-transplant (not shown). The calculated HOMA-IR (FIG. 4C) and response to a pyruvate tolerance test (not shown) were also attenuated in mice receiving trained scWAT, providing further evidence for enhanced insulin sensitivity. Transplantation of scWAT from trained and sedentary mice was not associated with changes in body weight, food intake, or spontaneous activity (not shown). Energy expenditure was increased (not shown) and respiratory exchange ratio (RER) was significantly decreased in the fasted state of mice receiving scWAT from sedentary (FIG. 4D), indicating a preference for fatty acids as fuel. Taken together, all of these data clearly demonstrate that transplantation of exercise-trained adipose tissue has marked beneficial effects on systemic glucose homeostasis.

The Beneficial Effects of Transplanting Trained scWAT are Short-Lived.

The effect of transplanting trained scWAT on glucose tolerance was short lived, as the effect was not as pronounced at day 14, and there was only a tendency for improved glucose tolerance at 28 days post-transplant (FIG. 4B). These data raise the possibility that the trained scWAT secretes factors that mediate the effects on glucose tolerance.

To determine if the effects of transplanting trained scWAT were specific to the location of the transplant, trained and sedentary scWAT was transplanted into the flank region, placed directly atop the inguinal adipose tissue. The scWAT (0.85 g) was divided in half, with one half being placed atop each endogenous adipose tissue pad. After nine days, mice transplanted with trained scWAT in the subcutaneous cavities had a significant improvement in glucose tolerance compared to both Sham and mice receiving sedentary scWAT (22% decrease in GTT AUC; P<0.01). Thus, transplantation of trained scWAT into both the visceral and subcutaneous cavity improves glucose tolerance. In an additional experiment, and in contrast to the effects of transplanting trained scWAT, there was no difference in glucose tolerance in mice transplanted with visceral WAT from trained or sedentary mice compared to sham controls.

Transplantation of scWAT Increases Glucose Uptake in Skeletal Muscle and Brown Adipose Tissue.

To begin to understand the mechanism for the improvement in glucose tolerance in mice receiving trained scWAT, in vivo glucose disposal was measured in a separate cohort of mice. Mice were injected with [$^3$H]-2-deoxyglucose in saline (Basal) or a 20% glucose solution that results in a physiological insulin release (54-56). In the 45 min following injection, glucose and insulin concentrations were significantly lower in mice transplanted with trained scWAT, demonstrating enhanced insulin sensitivity (not shown). Muscles, heart, and brown adipose tissue were removed and glucose uptake was determined. Under basal conditions there was no difference in glucose uptake among groups in any tissue. However, insulin-stimulated glucose uptake in the tibialis anterior (57% oxidative fibers) and soleus (95% oxidative) muscles was significantly increased in mice transplanted with trained scWAT, whereas this effect was not present in the more glycolytic muscles, gastrocnemius (40% oxidative) and extensor digitorum longus (EDL) (30% oxidative) (57,58). Interestingly, there was also an increase in glucose uptake in intrascapular brown adipose tissue, but not in the heart. These data demonstrate that transplanted scWAT from exercise-trained mice exerts beneficial effects on more oxidative skeletal muscles and brown adipose tissue, and raise the possibility that the trained adipose tissue communicates with other tissues.

Do Transplanted Exercise-Trained Adipocytes Function as Metabolic "Sponges"?

One interpretation of the improved whole-body and tissue glucose homeostasis with transplantation of trained scWAT is that the transplanted tissue from trained mice functions as a "sponge" or "sink" to remove and oxidize circulating glucose and lipids. If this is the major mechanism, the effects of transplantation on skeletal muscle and brown adipose tissue would be secondary to the decrease in circulating factors. Consistent with this hypothesis, exercise training decreases adipocyte size (4,38) and thus transplantation of trained scWAT could stem from the recipient mice receiving an increased number of adipocytes compared to mice transplanted with large cells from sedentary mice. To test this hypothesis we used a new cohort of mice and glucose tolerance was compared in mice transplanted with trained scWAT from 12 wk old mice, sedentary scWAT from 12 wk old mice, or sedentary scWAT from 6 wk old mice with a similar cell size to that of the trained mice. In another experiment, we measured basal and insulin-stimulated glucose uptake in vivo into the transplanted adipose tissue and found no difference in glucose uptake between the transplanted adipose tissue from the trained and sedentary mice. These data demonstrate that the trained adipose tissue does not function as a metabolic "sponge", at least not for glucose.

Transplantation of Trained scWAT Ameliorates the Effects of a High-Fat Diet.

We have recently studied an entirely new cohort of mice to test the hypothesis that transplantation of trained scWAT would improve glucose homeostasis under conditions of metabolic stress. Recipient mice were fed either a standard chow (21% kcal from fat) or a high-fat diet (60% kcal from fat; Research Diets) for 6 wks, followed by transplantation of either scWAT from sedentary or trained mice. At nine days post-transplant there was a significant improvement in glucose tolerance in mice receiving both trained and sedentary scWAT, although the effect was more pronounced in the mice transplanted with trained scWAT (65% decrease in GTT AUC compared to sham high-fat fed; $P<0.006$). In fact, mice receiving trained scWAT had glucose tolerance comparable to chow fed mice, thus fully ablating the deleterious effect of the high-fat diet.

Example 2

Identification of Transplanted Factors

Exercise Training Results in Remodeling of scWAT.

The remarkable effects of the trained adipose tissue on glucose homeostasis and the accompanied increase in skeletal muscle and brown adipose tissue glucose uptake suggest that training results in marked adaptations to scWAT. To begin to understand the mechanism for the effects of training on adipose tissue we used microarray analysis to compare the gene expression profile of scWAT obtained from a cohort of mice that were housed in wheel cages for 11 days (Train) or remained sedentary (Sed). Using criteria of $P<0.05$ and $Q<0.05$, exercise training had profound effects on the expression profile of the scWAT with 1549 genes significantly increased by training and 1156 genes significantly down-regulated by training. This vast number of genes altered in the trained scWAT demonstrates that there is remarkable adaptation in this tissue. In fact, although a direct comparison cannot be made, the number of genes up-regulated by exercise training in scWAT is substantially greater than what has been reported to be increased in skeletal muscle with exercise training (59-62). Gene Set Enrichment Analysis (GSEA; $P<0.05$ and $Q<0.25$) determined that exercise training resulted in significant increases in genes involved in metabolism, mitochondrial biogenesis, oxidative stress and signaling, membrane transport, cell stress, proteolysis, apoptosis, and as will be discussed in more detail below, secreted proteins.

We also performed morphological and biochemical characterization of the trained scWAT and a pronounced molecular characteristic of the scWAT from the trained mice is a clear "browning" effect. Briefly, we found that trained scWAT have: 1) the induction of numerous brown adipocyte marker genes (e.g., Prdm16, Ucp1, Pgc1a, Elovl3, Cidea); 2) increased Ucp1 staining; 3) a multilocular appearance; and 4) an increased basal rate of oxygen consumption measured by Seahorse (588±20 vs 657±15 pmoles/min; $P<0.01$). In addition to these mouse studies, in collaboration with the Pedersen laboratory (Copenhagen), we obtained scWAT samples from human subjects before and after 12 weeks of intensive exercise training. Training significantly increased UCP1 mRNA (not shown), demonstrating the physiological relevance of the mouse findings to humans. Our mouse data are consistent with recent reports showing that four weeks of exposure to an enriched environment, which included the presence of a running wheel, increased brown adipose tissue markers (63), and in another study wheel running and swim exercise significantly increased Ucp1 mRNA levels (5). The mechanism for these effects was reported to result from increases in hypothalamic BDNF (63) or the myokine irisin (5), respectively. The development of brown fat-like adipocytes in white adipose tissue also occurs in response to cold exposure (35) and β3-selective adrenergic agonists (29), and thus a number of different stimuli result in a browning of white adipose tissue. While the mechanism for the browning effect by exercise and other stimuli is being studied by many other laboratories, our work will instead focus on the effects of trained scWAT to mediate metabolism and to alter the adipokine profile.

To identify factors that mediate the striking effects of trained adipose tissue on skeletal muscle and whole-body metabolism, we have performed detailed molecular characterization of exercise-trained subcutaneous white adipose tissue. Factors were identified by using microarray, PCR and histological techniques know to those of ordinary skill in the art. Remarkably and unpredictably, it was found that exercise training of mice for only 11 days significantly increased the expression of >1500 genes in subcutaneous white adipose tissue. This included significantly increased expression of 55 genes encoding secreted proteins. (See, FIGS. 2 and 3). Furthermore, studies comparing exercise-trained adipose tissue from human subjects support the mouse data and comparative analysis of these data sets has led us to identify several novel candidates for investigation as putative therapeutic agents (FIG. 3). While some of these proteins have been characterized in other cell systems and implicated in various diseases, few have been studied in adipose tissue.

Identification of Secreted Proteins from scWAT Significantly Altered by Exercise Training.

The adipocyte secretome has been investigated in the context of diabetes and metabolic disease (64), but studies of exercise regulation of adipokines have been limited (65). As mentioned above, our array analysis shows that exercise training has profound effects on scWAT from the mouse, including changes in the expression of secreted proteins. Working with the Boston University/Joslin Computational Core laboratory, secreted proteins were identified from the overall list of significant genes (described above) using three databases: Secreted Protein Database (SPD), Gene Ontology (GO), and Ingenuity Extracellular, all of which are known to those of skill in the art. Comparing scWAT from trained versus sedentary mice, genes encoding 55 secreted proteins were significantly increased and 217 were significantly decreased. Interestingly, none of the well-established adipokines were on these lists showing limited effects of exercise training on known adipokines.

To search for the most relevant genes, we cross-referenced our mouse and human microarray databases. For this purpose, statistical analysis was performed using Microsoft Access, Excel, and R/Bioconductor (www.bioconductor.org), as well as a web application developed in conjugation with the BU/Joslin Computational Core. Approximately 100 transcripts were significant in both mouse and human samples. Based on public databases of adipose tissue gene profiles, we have identified a number of top candidates, including: transforming growth factor beta 2 (TGFβ2), cysteine-rich secretory protein-1 (CRISP-1), apo-lipoprotein M (APOM), brevican (BCAN), transcobalamin 2 (TCN2) and wingless-type (WNT3a). We have confirmed by RT-PCR and/or Western blotting that these candidates are expressed in scWAT and increased with exercise training. Interestingly, these genes have not been previously characterized as adipokines, increasing the novelty of the present invention. Moreover, most of these proteins have been implicated in some aspect of metabolism, cell transport, or cell signaling (66-69).

TGFβ2 and CRISP-1 are Putative Adipokines Regulated by Exercise Training in scWAT.

One candidate adipokine is TGFβ2. TGFβ2 is a glycosylated protein that has been implicated in developmental biology (70,71) and in extracellular matrix function of the eye (72), but its potential role as an adipokine has not been explored before this research. Our array data demonstrate that exercise training significantly increases TGFβ2 gene expression in mouse and human scWAT. In addition, exercise training for 11 days in the mouse significantly increased both TGFβ2 mRNA and protein in scWAT (FIGS. 7A & B). Our preliminary data shows that transplantation of trained scWAT increases glucose uptake into skeletal muscle and brown adipose tissue in vivo. Thus, to determine if TGFβ2 increases glucose uptake in skeletal muscle cells and brown adipocytes, we incubated differentiated C2C12 myotubes and WT-1 brown adipocytes with recombinant TGFβ2 for 4 or 24 hours at 20 ng/ml (dose based on dose response experiment; not shown). TGFβ2 incubation significantly increased basal and insulin-stimulated glucose uptake in both cell types at both time points (FIGS. 7C & D; only 24 hr data shown). The increases in glucose uptake occurred in the absence of changes in glucose transporter expression (not shown). FIG. 6 shows that incubation of intact skeletal muscle with TGFβ2 increases glucose uptake. These exciting data support the inventive conception that TGFβ2 mediates the effects of trained scWAT on glucose homeostasis.

Five additional adipokines identified herein will provide comparable data. CRISP-1 is a secreted glycoprotein which belongs to the CAP super-family. CRISP-1 has been primarily studied in the context of epididymal maturation; however, a recent report shows that CRISP-1 is also highly expressed in multiple tissues including skeletal muscle, thymus, and uterus (adipose was not studied) (69), increasing the likelihood that CRISP-1 has a broader role in mammalian physiology. Our preliminary data show that Crisp-1 mRNA is highly expressed in mouse scWAT relative to other tissues, and using 3T3-L1 adipocytes, we found that CRISP-1 increases during differentiation. mRNA expression of Crisp-1 was significantly increased by ~6-fold in scWAT of trained mice, but there was no increase in Crisp-2, -3, and -4 mRNA expression. BCAN is a brain-specific chondroitin sulfate proteoglycan (CSPG). The roles of CSPGs in the central nervous system and during development are well established, however their role in adipose tissue function, as well as response to exercise, were not known until this work. Our preliminary data show that Bcan mRNA is significantly increased with training in mouse scWAT, and increased during differentiation in 3T3-L1 adipocytes. Acorn is a member of the lipocalin superfamily that is expressed in liver, kidney and adipose tissue (66,73). Plasma APOM is reduced in the metabolic syndrome and is an anti-atherogenic protein (66). In addition to increases in the APOM gene in mouse and humans with exercise training, our preliminary data show that APOM protein and mRNA are expressed in mouse and human scWAT, respectively. TCN2 is expressed in various tissues, including adipose tissue and, among other functions, is important for normal nervous system regulation. Exercise training increased Tcn2 mRNA in the mouse and our preliminary data show that training increases TCN2 in scWAT. WNT3a—the WNT gene family consists of structurally related genes which encode secreted signaling proteins. These proteins have been implicated in oncogenesis and in several developmental processes, including regulation of cell fate and patterning during embryogenesis. This gene is a member of the WNT gene family. It encodes a protein which shows 96% amino acid identity to mouse Wnt3A protein, and 84% to human WNT3 protein, another WNT gene product. This gene is clustered with WNT14 gene, another family member, in chromosome 1q42 region. FIGS. 10 and 11 show that WNT3a incubation increases glucose uptake in C2C12 muscle cells and 3T3L1 adipose cells. Experiments were conducted as outlined elsewhere in this specification.

Example 3

Characterize and Validate Effects of Selected Secreted Proteins on Glucose Uptake Glucose Uptake in Muscle and Adipose Cell Lines—

We will perform studies to measure glucose uptake and glucose transporter expression (GLUT1/4) in C2C12 muscle cells, 3T3L1 adipocytes, and WT-1 brown adipocytes. All three cell lines are currently used in the Goodyear laboratory. Recombinant proteins will be purchased from commercial sources. Differentiated cells will be incubated in the presence or absence of selected proteins at various concentrations. Incubation times will range from 30 min for study of short term effects on glucose uptake and up to 48 hours to determine long term effects on both glucose uptake and glucose transporter expression. Glucose uptake. GLUT1, and GLUT4 protein expression will be measured using standard procedures from our laboratory. Glucose uptake will be measured in the basal state, with submaximal insulin, and with maximal insulin. Proteins that have positive effects on glucose uptake and/or transporter expression will be investigated further as detailed below.

The proteins to be studied have been prioritized based on expression level in adipocytes, degree of increase with exercise training, demonstration of protein or mRNA expression in humans, and literature reports of protein function in other tissues. We are actively studying 8-10 secreted proteins based on these criteria.

Isolated Mouse Skeletal Muscles—

We have established models for studies of the effects of various hormones and compounds on rates of glucose uptake in rodent skeletal muscles. For this purpose, muscles composed of various fiber types [e.g. soleus, extensor digitorum longus (EDL)] will be obtained from mice and incubated with the candidate protein at various doses and for various incubation times ranging up to 4 hours. Basal and insulin-stimulated glucose uptake will be measured, as well as GLUT4 protein expression. Depending on the outcome of these experiments, we can measure the effects of the candidate protein on insulin signaling, AMPK signaling, and the energy status of the muscles. This study will determine if the candidate secreted protein has direct effects on glucose uptake in skeletal muscle. Based on the outcomes we may also choose to determine the effects of the proteins on glucose uptake in primary white and brown adipocytes.

Candidate proteins will be further screened and selected based drug-ability characteristics, available data on (human) toxicity and amenability for production and development as a therapeutic.

Example 4

Characterize and Demonstrate In Vivo Treatment Effect with the Candidate Protein(s) in the Improvement of Systemic and Peripheral Metabolism From Example 3, drug candidates will be selected to determine the effects on whole-body and tissue glucose metabolism. For these experiments, recombinant proteins will be generated by subcloning the specific adipokine cDNA along with a flag-tag into a constitutive expression vector such as pCMV6 (the procedures of which are known to those of ordinary skill in the art). The vector will be overexpressed in, for example, 293 HEK cells (or other suitable cells) and the overexpressed protein purified. As an alternative to recombinant adipokine production, we can employ an adenoviral system (AAV1). Adenovirus will be generated, injected through the tail vein, resulting in overexpression and secretion from liver. By this method, sufficient amounts of recombinant protein will be expressed.

To study the physiological response to the adipokine, 12 wk old male mice will be treated with vehicle or the candidate protein for 1, 5, 9, 14, or 28 days (for example). Using recombinant protein expression vectors, treatment will be by i.p. injection, two times per day. The dose will be based on the plasma concentrations of the adipokine in trained mice. To study whole-body glucose homeostasis, mice will undergo glucose tolerance tests, insulin tolerance tests, and euglycemic-hyperinsulinemic clamp studies. We will also measure circulating insulin, triglycerides, free fatty acids, cholesterol, and several established adipokines. Mice will also be housed in metabolic chambers to assess energy expenditure, physical activity, RER, etc. To determine if the selected adipokine have tissue-specific effects, skeletal muscles, brown adipose tissue, and liver will be obtained from the treated mice and used to measure glucose uptake, fatty acid uptake and oxidation, intracellular signaling pathways, and the expression and/or activity of key metabolic proteins, as described throughout this application.

Based on the effect of the adipokines on increasing or decreasing glucose homeostasis, one or more will next be tested using animal models of obesity and diabetes, such as the high-fat fed mouse. These experiments will determine the effects of the novel adipokines on systemic and tissue metabolic homeostasis.

The goal of Example 4 is to complete characterize protein candidates in the animal models to help facilitate and design human studies in glucose control.

In view of the teachings of the present specification, one of ordinary skill in the art will be able to identify and characterize novel and nonobvious protein targets as effective therapeutic treatments for type 2 diabetes and other metabolic disorders related to glucose tolerance without undue experimentation.

Prophetic Exemplification

Example 1

This Experiment Will Determine if scWAT from Exercise-Trained Mice has Endocrine Effects on Skeletal Muscle Metabolism, Signaling, Mitochondrial Markers, and Fiber Type The data presented herein show that training-induced adaptations to scWAT function to improve glucose tolerance and skeletal muscle glucose uptake in vivo. These experiments will follow-up on the data presented here by determining the mechanism by which "trained" adipose tissue exerts effects on whole-body and skeletal muscle metabolic homeostasis.

Experiment 1a

The Effects of Transplanting Trained Subcutaneous Adipose on Skeletal Muscle Glucose Uptake In Vivo are Preserved In Vitro The rapid time course for improved glucose homeostasis and skeletal muscle glucose uptake with transplantation of trained scWAT indicates that the underlying mechanism mediating this effect stems from secretion of adipokines from the trained scWAT. This likely results from direct, short term acute effects of the putative adipokines on the muscle and/or from adipokine-mediated chronic adaptations to muscle. It will be shown that transplantation of scWAT results in chronic adaptations to skeletal muscle and what, if any, circulating factors are necessary for the increase in muscle glucose uptake observed in vivo. It will also be shown that transplantation of scWAT from exercise-trained mice will increase skeletal muscle glucose uptake in vitro compared to muscles of mice receiving scWAT from sedentary mice and sham treated mice.

Experimental Methods:

Briefly, scWAT (0.85 g) will be removed from 11 day trained or sedentary control mice and transplanted into the visceral cavity of age-matched sedentary recipient mice. Sham operated mice will serve as additional "recipient" controls. Body weights and food intake will be measured every two days post-transplant. Both soleus and EDL muscle will be studied, since these muscles have different fiber type composition and were shown to respond differently to transplantation in vivo. Nine days after transplantation, soleus and EDL muscles from the recipient mice will be isolated and pre-incubated for 40 min in standard Krebs buffer with multiple buffer changes in order to wash out any potential systemic factors. Glucose uptake will be measured in the basal state and in response to submaximal and maximal insulin concentrations using our standard method (74). If glucose uptake is enhanced, this will indicate that transplantation of trained adipose tissue causes chronic adaptations to the skeletal muscle.

Experiment 1 b

Transplantation of scWAT from Trained Mice Enhance Intracellular Signaling and the Metabolic Profile of Skeletal Muscle To begin to elucidate the mechanism for enhanced glucose uptake in skeletal muscle, it will be shown that there are changes in key muscle signaling or metabolic proteins. It will also be shown that transplantation of scWAT from exercise-trained mice will increase skeletal muscle insulin signaling, mitochondrial markers, the percentage of oxidative fiber types, and the number of muscle capillaries.

Experimental Methods:

Cohorts of mice will be transplanted as described and nine days post-transplantation, mice will be studied in the basal state or 10 min following maximal insulin stimulation via i.p. injection, as we have performed (75, 76). Soleus, tibialis anterior, EDL, and gastrocnemius muscles, representing muscles composed of varying fiber types, will be used to measure insulin receptor, IRS, Akt, AS160, and TBC1D1 expression and phosphorylation using our methods (76-80). GLUT4, GLUT1, and hexokinase II expression will be measured by Western blotting, and glycogen, triglyceride, ceramide content, and multiple mitochondrial markers including citrate synthase activity, NADH cytochrome C reductase, PDH, and SDH by biochemical assays (81,82). RT-PCR will be used to determine expression of mitochondrial components for electron transfer (COX II and IV), as we have described (83). Fiber type will be determined by electrophoretic separation of MHC isoforms (81, 84) and staining of fixed muscle sections (85). Fixed muscle sections will be used to analyze muscle capillary density (capillaries/mm$^2$) based on CD31 immunofluorescence (86, 87). These studies will determine the underlying metabolic phenotype of the skeletal muscles from mice transplanted with trained adipose tissue which will include insulin signaling, mitochondrial markers, the percentage of oxidative fiber types, and the number of muscle capillaries, and the mechanism for lack of effect in the less oxidative muscles.

Experiment 1c

Transplantation of scWAT from Trained Mice Enhance Skeletal Muscle Fatty Acid Uptake and Oxidation in Recipient Animals Mice transplanted with trained scWAT have a decrease in RER, suggesting increased whole-body fatty acid utilization. Due to its large mass, muscle consumes a large amount of free fatty acids. It will be shown that transplantation of trained scWAT will alter fatty acid metabolism in the muscle of recipient mice. It will also be shown that skeletal muscles from mice transplanted with trained adipose tissue will have increased fatty acid uptake and oxidation, and altered expression and/or activity of proteins regulating fatty acid metabolism.

Experimental Methods:

Cohorts of mice will be transplanted as described above and studied nine days later. Mice will be fasted for five hours, anesthetized, followed by injection (i.v.) of a bolus of [9,10-$^3$H] palmitate and [$^{14}$C] mannitol (88). Rates of fatty acid uptake will be measured in soleus, tibialis anterior, EDL, and gastrocnemius muscles. To determine if putative effects on fatty acid uptake are preserved in vitro, soleus and EDL muscles will be used for in vitro incubation. Both fatty acid uptake and oxidation will be measured using [1-$^{14}$C] palmitate as we (89) and others described (90,91). Muscles obtained in the basal state from Experiment 1b will be used to determine AMPK and ACC phosphorylation and activity, malonyl co-A concentrations, CPT-1 expression and activity, and lipoprotein lipase, FATBP, FATP1, CD36, and ATGL expression (92,93).

Experiment 1d

Factors Secreted from the scWAT of Exercise-Trained Mice Regulate Skeletal Muscle Glucose Uptake and/or Fatty Acid Oxidation Our preliminary data indicates that exercise training stimulates cross-talk between scWAT and skeletal muscle. Another approach that can be used to determine if trained scWAT regulates skeletal muscle glucose uptake will be to incubate muscles with adipose tissue-conditioned media (37). Depending on the outcome of the fatty acid metabolism studies (Experiment 14 it will also be shown the effects of conditioned media on fatty acid uptake and oxidation. It will also be shown that incubation with sedentary scWAT-conditioned media will reverse the beneficial effects of exercise training on skeletal muscle. It will further be shown that i) Incubation of skeletal muscles with conditioned media from trained scWAT will increase rates of glucose uptake, fatty acid uptake and oxidation compared to muscles incubated with sedentary scWAT; ii) Incubation of trained skeletal muscles with conditioned media from sedentary scWAT will decrease rates of glucose uptake, fatty acid uptake and oxidation compared to muscles incubated with sedentary scWAT.

Experimental Methods:

scWAT from trained and sedentary mice will be dissected into 10- to 15-mg fragments. Fragments will be washed, incubated and rotated gently for 3-5 h. Tissue will be removed by centrifugation, and the aqueous layer filtered through a 0.2-µm membrane. The medium will be concentrated 16- to 80-fold at a 1-kDa cutoff in an ultrafiltration cell, and protein concentration determined. The conditioned adipocyte medium can be used immediately or frozen and used for later experiments (94). Soleus and EDL muscles isolated from control mice and mice trained for 11 days in wheel cages will be incubated with the conditioned media for 1, 2, or 4 hrs. Glucose uptake, fatty acid uptake, and fatty acid oxidation will be measured as described above. If incubation of skeletal muscle with conditioned media from trained mice has effects on glucose and/or fatty acid metabolism, this will support the hypothesis that there are adipokines released from exercise-trained scWAT that directly alter skeletal muscle substrate metabolism. Incubation of trained skeletal muscle with scWAT from sedentary mice reverses the beneficial effects of training anbd this will show that adipose tissue from sedentary mice can have detrimental effects on muscle metabolism. Alternatively, we will obtain scWAT from high fat-fed mice and show that this tissue has detrimental effects on muscle.

Experiment 1e

The Stromal Vascular Fraction (SVF) and/or Adipocytes from Trained scWAT Regulate Skeletal Muscle Glucose Uptake and/or Fatty Acid Oxidation Rationale:

Although approximately 80% of adipose tissue is thought to be composed of mature adipocytes, the stromal vascular fraction (SVF) of adipose tissue is also a significant component of this tissue. The SVF is composed of multiple cell types including preadipocytes, mesenchymal stem cells, endothelial progenitor cells, macrophages, and immune cells. It will be shown that the SVF is a source for the beneficial effects of scWAT on glucose metabolism in skeletal muscle. It will also be shown that incubation of skeletal muscles with SVF and adipocytes from trained scWAT will increase rates of glucose uptake and fatty acid uptake/oxidation compared to SVF and adipocytes from sedentary scWAT.

Experimental Methods:

scWAT from trained and sedentary mice will be dissected, minced into small pieces in DMEM growth media, and digested with collagenase A (0.1 mg/mL) at 37° C. for 15 min or until cells are dispersed (95). Adipocytes will be isolated and cultured, and the remaining media and pellet (SVF) will be filtered through a 100 µM filter and rinsed with DMEM. The pellet will be incubated for 2 min with erythrocyte lysis buffer, and then resuspended in PBS. Soleus and EDL muscles from control mice and mice trained for 11 days in wheel cages will be incubated with the isolated adipocytes or SVF for 1, 2, or 4 hrs. Glucose uptake, fatty acid uptake, and fatty acid oxidation will be measured as described above.

Alternative Approaches for Prophetic Example 1

For prophetic Experiments 1d & e, it is possible that longer periods of incubation with the conditioned media may be required to affect glucose uptake or fatty acid oxidation. If so, one alternative will be to incubate muscles for periods of up to 8 hours. This prolonged incubation will require changing media at the 4 hr time point, including the generation of fresh scWAT-condition media, adipocytes, and SVF. Another alternative approach would be to use C2C12 muscle cells, as we have described in preliminary data, which will allow for much longer incubation times. We have successfully used these cells to measure both glucose uptake and fatty acid oxidation.

Prophetic Example 2

To Determine the Role of Brown Adipose Tissue and Liver in the Beneficial Effects of Transplanting scWAT on Glucose Homeostasis Given the pronounced effects of transplanting scWAT on systemic glucose homeostasis, it is likely that multiple tissues are affected by the exercise-trained adipose tissue. Consistent with this hypothesis, our preliminary data demonstrate that in vivo rates of glucose uptake are increased in brown adipose tissue from mice transplanted with scWAT. The liver is a critical mediator of glucose tolerance and insulin action, making it likely that transplanting trained scWAT also has beneficial effects on liver metabolism.

In addition to investigating the effects of transplanting trained scWAT on brown adipose tissue and liver, substrate utilization of the transplanted adipose tissue itself will also be investigated. This is important because while we have considerable data showing that the beneficial effects of transplanting trained adipose tissue has on glucose homeostasis are mediated by adipokines, the transplanted adipose tissue from trained mice may also function as a "sponge" or "sink" to remove and oxidize circulating glucose and lipids.

Experiment 2a

The Effects of Transplanting Exercise-Trained scWAT on Endogenous Brown Adipose Tissue Metabolism Transplantation of trained scWAT resulted in a significant increase in glucose uptake in the endogenous brown adipose tissue of recipient mice. In this experiment, we will use similar methods described prophetic Example 1, above, for the study of skeletal muscle metabolism in order to determine if chronic adaptations or acute stimuli are responsible for the enhanced glucose uptake in brown adipose tissue, to study fatty acid metabolism, and to determine the molecular characteristics of the brown adipose tissue. It will be shown that compared to mice receiving scWAT from sedentary mice, the endogenous brown adipose tissue from mice transplanted with scWAT from exercise-trained mice will have: increased glucose uptake and metabolism in vitro; increased fatty acid uptake and oxidation; and increased rates of oxygen consumption.

Experimental Methods:

The transplantation method and experimental groups are described in prophetic Example 1, above. Nine days after transplantation, brown adipose tissue from the recipient mice will be removed, weighed, and placed in Krebs-bicarbonate-Hepes buffer. Brown adipose cells will be isolated using 2 mg/ml collagenase (95, 96). Cells will be pre-incubated for 40 min with multiple buffer changes in order to wash out any potential systemic factors. Glucose uptake will be measured in the basal state and in response to submaximal and maximal insulin (37). Fatty acid metabolism will be measured both in vivo and in vitro. For the in vivo measurement, the same cohorts of mice used in Experiment 1c, above, will be used to measure fatty acid uptake in intrascapular brown adipose tissue. To determine if putative effects of exercise-trained scWAT on brown adipocyte fatty acid metabolism are preserved in vitro, adipocytes will be isolated as described above and both fatty acid uptake and oxidation will be measured using conversion of $[1-^{14}C]$ palmitate into $CO_2$ (91,97,98).

Oxygen consumption rate will be measured in brown adipose tissue using a Seahorse Analyzer (99) as we have used for white adipose tissue (see, above) (1,100). Briefly, adipose tissue (5×10 µg tissue/mouse) will be placed on mesh screen circles and "snapped" into a well of an Islet plate, and 500 µl of DMEM with low glucose will be placed in each well. Plates will be equilibrated without $CO_2$, and then basal oxygen consumption rate will be measured. Samples will be incubated with various carbohydrate and lipid substrates to stimulate oxygen consumption, and then treated with oligomycin to inhibit oxygen consumption. These studies will show that scWAT from exercise-trained mice will improve the metabolic phenotype of the brown adipose tissue, which could have significant metabolic consequences given the recent recognition of the importance of brown adipose tissue in regulating metabolism (101).

Experiment 2b

Livers from Mice Transplanted with scWAT from Exercise-Trained Mice have an Improved Metabolic Profile Transplantation of scWAT from exercise-trained mice results in marked improvements in glucose tolerance and pyruvate tolerance, both indicative of enhanced liver function. It will be shown that livers from mice transplanted with trained scWAT will have increased insulin sensitivity, decreased hepatic glucose output, and decreased hepatic lipid concentrations.

Experimental Methods:

Initial assessment of liver function will be done by euglycemic-hyperinsulinemic clamp studies in conjunction with the Joslin Animal Physiology Core Laboratory. Simultaneously with scWAT transplantation, surgery will also be performed to implant catheters in the mice. The clamp procedure will be done nine days post-surgery using standard procedures (102). Liver triglyceride, diacylglycerol, and ceramide concentrations will be measured by biochemical assay (81,103,104), and triglyceride concentrations will also be measured by Oil Red O staining of liver sections. Liver sections will also be stained to assess monocyte infiltration and steatosis. Oxygen consumption rate will be measured in liver sections using the method described above for brown adipose tissue. These experiments will elucidate the liver phenotype, as well as assessing whole-body insulin sensitivity.

Experiment 2c

Secreted from the scWAT of Exercise-Trained Mice Regulate Brown Adipocyte Metabolism and Hepatic Insulin Sensitivity Prophetic Experiments 2a and 2b will determine the effects of transplanting exercise-trained scWAT on the metabolic phenotype of the brown adipose tissue and liver. Our preliminary data indicates that exercise training stimulates cross-talk between scWAT and both endogenous brown adipose tissue and liver. For this experiment we will show factors secreted from trained scWAT directly regulate brown adipocyte and hepatocyte function. Insulin suppressed glucose production by 63.5% and glucagon stimulated glucose output by 6-fold in the primary mouse hepatocytes. It will be shown that incubation of brown adipocytes and hepatocytes with conditioned media from adipose tissue from trained mice will increase insulin sensitivity, increase fatty acid uptake, and increase fatty acid oxidation.

Experimental Methods:

For these experiments, hepatocytes and brown adipocytes isolated from control mice will be incubated for 1, 2, or 4 hours in media conditioned with trained or control scWAT as described in prophetic Experiment 1d, as well as SVF as described in prophetic Experiment 1e. To assess hepatocyte glucose output, hepatocytes will be stimulated with various concentrations of insulin or glucagon, and glucose production into the media will be measured (92). For both hepatocytes and brown adipocytes, we will also perform pulse-chase experiments using $^{14}$C-oleate to measure triglyceride turnover, triglyceride secretion, and fatty acid oxidation (105). For brown adipocytes, both fatty acid uptake and oxidation will be measured using the conversion of [1-$^{14}$C] palmitate into $CO_2$ (91, 97, 98) and glucose uptake and metabolism will be measured in the basal state and in response to submaximal and maximal insulin at each time point (37).

Experiment 2d

Transplanted scWAT from Trained Mice have Increased Fatty Acid Metabolism

Transplanted trained scWAT could also act as a "sink" to remove and oxidize circulating glucose and lipids, resulting in improved systemic and tissue function. However, our preliminary data show that the trained adipose tissue does not function as a sink to remove glucose, since rates of glucose uptake are not elevated in the transplanted trained scWAT. Multiple findings from our data indicate that enhanced fatty acid metabolism in the transplanted trained adipose tissue: 1) mice transplanted with trained adipose tissue have a slight, but significant decrease in whole-body RER; 2) Seahorse analysis shows that exercise-trained scWAT has a significant increase in basal oxygen consumption rate (OCR); and 3) microarray experiments show increased expression of numerous fatty acid metabolism genes in the trained scWAT. It will be shown that transplanted trained scWAT will have increased fatty acid uptake and oxidation, and increased expression of key markers of fatty acid metabolism compared to mice transplanted with sedentary scWAT.

Experimental Methods:

Cohorts of mice will be transplanted as described in the previous section and studied nine days later. Mice will be fasted for five hours, anesthetized, and injected i.v. with a bolus of [9,10-$^3$H] palmitate and [$^{14}$C] mannitol, and the transplanted scWAT dissected and used to measure fatty acid uptake in vivo (88). Tissues will be obtained from the mice used for Experiment 1c and the endogenous visceral and scWAT, as well as brown adipose tissue, will be studied and used to compare with the transplanted adipose tissue. We will also measure fatty acid uptake and oxidation in isolated adipocytes from transplanted scWAT from trained and sedentary mice (37) using [1-$^{14}$C] palmitate with procedures we (89) and others have previously described (37,90,91). To determine if the transplanted trained scWAT have an increase in key fatty acid regulatory proteins we will use tissues obtained from animals described in Experiment 1b. The transplanted scWAT will be used to determine AMPK phosphorylation and activity, ACC phosphorylation and activity, malonyl co-A concentrations, CPT-1 expression and activity, and lipoprotein lipase, FATBP, FATP1, CD36, and ATGL expression (92,93). Fixed sections of the endogenous visceral white adipose tissue, endogenous scWAT, and brown adipose tissue will also be stained to determine if monocyte infiltration and cell size may be altered in these tissues from mice transplanted with scWAT. Taken together, these studies will determine the metabolic phenotype of the transplanted tissue and if these cells function as a metabolic sink.

Prophetic Example 3

To Determine the Function of Novel Adipokines Derived from the scWAT of Exercise-Trained Mice The data provided in this specification show that transplantation of scWAT from exercise-trained mice into sedentary mice rapidly improves glucose tolerance and increases skeletal muscle and brown adipose tissue glucose uptake. These findings indicate that trained scWAT secretes factors that have beneficial effects on whole-body and tissue metabolism. Exercise-trained scWAT may also have blunted secretion of adipokines that negatively regulate glucose homeostasis. Array analysis showed that >250 genes encoding secreted proteins are significantly increased or decreased in trained scWAT. Candidate adipokines have been identified that are increased with exercise training. TGFβ2, CRISP-1, APOM, BCAN, and TCN2 have been identified as the most likely proteins to have metabolic effects.

Experiment 3a

Exercise Training Alters the Protein Expression of TGFβ2, CRISP-1, APOM, BCAN, and TCN2: The Time Course of Changes in these Putative Adipokines Following Transplantation; these Putative Adipokines Secreted from Isolated Adipose Tissue The microarray studies presented in this specification have identified genes encoding candidate adipokines that are increased or decreased by exercise training. It will be shown that TGFβ2, CRISP-1, APOM, BCAN, and TCN2 protein will be: expressed in scWAT; increased with exercise training; and detected in scWAT-conditioned media.

Experimental Methods:

Antibodies to putative adipokines have (or will be) purchased from commercial sources and validated for use in mouse tissues [TGFβ2 (Cell Signaling #8406), CRISP-1 (Santa Cruz; sc-21280), APOM (GeneTex; GTX88588), BCAN (R&D Systems; 4009-BC-050), and TCN2 (Abcam; ab113873)]. In the event that antibodies are not effective, we will order custom antibodies. One cohort of mice for this experiment will be trained or sedentary for 11 days and the scWAT transplanted into sedentary recipients as described in this application. As suggested by the reviewer, to assess the time course of changes in the adipose tissue with transplantation, scWAT and serum samples will be obtained 2, 4, 9, and 28 days post-transplant. TGFβ2, CRISP-1, APOM, BCAN, and TCN2 protein and serum concentrations will be measured by Western blotting and/or ELISA. Circulating adiponectin, leptin, resistin, TNF-α, IL-6, and other cytokines will be measured by the Joslin Specialized Assay Core Lab. A separate cohort of mice will be used to generate trained scWAT that will not be used for transplantation. Mice will be trained or sedentary for 2, 6, or 11 days and scWAT and serum obtained for Western blotting of candidate adipokines, as well as established adipokines. These two experiments will provide a detailed time course for the increased expression of adipokines with training, as well as determining the effects of transplantation on adipokine expression in the scWAT and serum.

In addition to determining the expression of TGFβ2, CRISP-1, APOM, BCAN, and TCN2 in whole scWAT lysates, expression in the SVF and isolated adipocytes from scWAT will be measured. Depending on the outcome of this study, we may determine if TGFβ2, CRISP-1, APOM, BCAN, and TCN2 are detected in media conditioned with whole tissue, SVF, and/or isolated adipocytes. In the event that the putative adipokine is not detectable, plasmid vectors containing the protein of interest with a tag on either the C-terminal or N-terminal to avoid proteolytic cleavage of one terminal prior to adipokine secretion, will be generated. Vectors will be expressed in 3T3 L1 cells and secretion into the media will be determined by blotting for the protein tag. We will also assess protein expression in multiple tissues throughout the body. Based on these findings, we will perform Western blotting of adipose and other tissues, as well as serum, in animal models of obesity and diabetes. These studies will show that TGFβ2, CRISP-1, APOM, BCAN, and TCN2 have altered expression under conditions of enhanced and impaired glucose homeostasis.

Experiment 3b

An Acute Bout of Exercise Will Cause Secretion of TGFβ2, CRISP-1, APOM, BCAN, and TCN2 and these Effects Enhanced in the scWAT of Exercise-Trained Mice The preliminary data show robust changes in gene expression with exercise training; the stimuli for release of these proteins may stem from an acute bout of exercise. It will be shown that a single bout of exercise causes TGFβ2, CRISP-1, APOM, BCAN, and TCN2 secretion from scWAT and this secretion is more pronounced in scWAT from exercise-trained mice.

Experimental Methods:

Two approaches will be used to address this question. First, both trained (wheel cages, 11 days) and sedentary mice will be exercised on a rodent treadmill for 1 h at 0.8 mile/hr up a 15% grade and blood samples will be obtained at multiple time points during and after exercise and used to assess adipokine concentration. The effects of a single bout of exercise will be studied since this is the normal physiological stimulus that would result in secretion of adipokines. For the other approach, both trained and sedentary mice will exercise and scWAT will be removed and incubated in vitro as described in prophetic Example 1. ELISAs and/or Western blotting will be used as described above to measure TGFβ2, CRISP-1, APOM, BCAN, and TCN2. We will show that an acute bout of exercise will stimulate adipokine secretion and that this effect will be greater in the trained mice.

Experiment 3c

Figure 5:
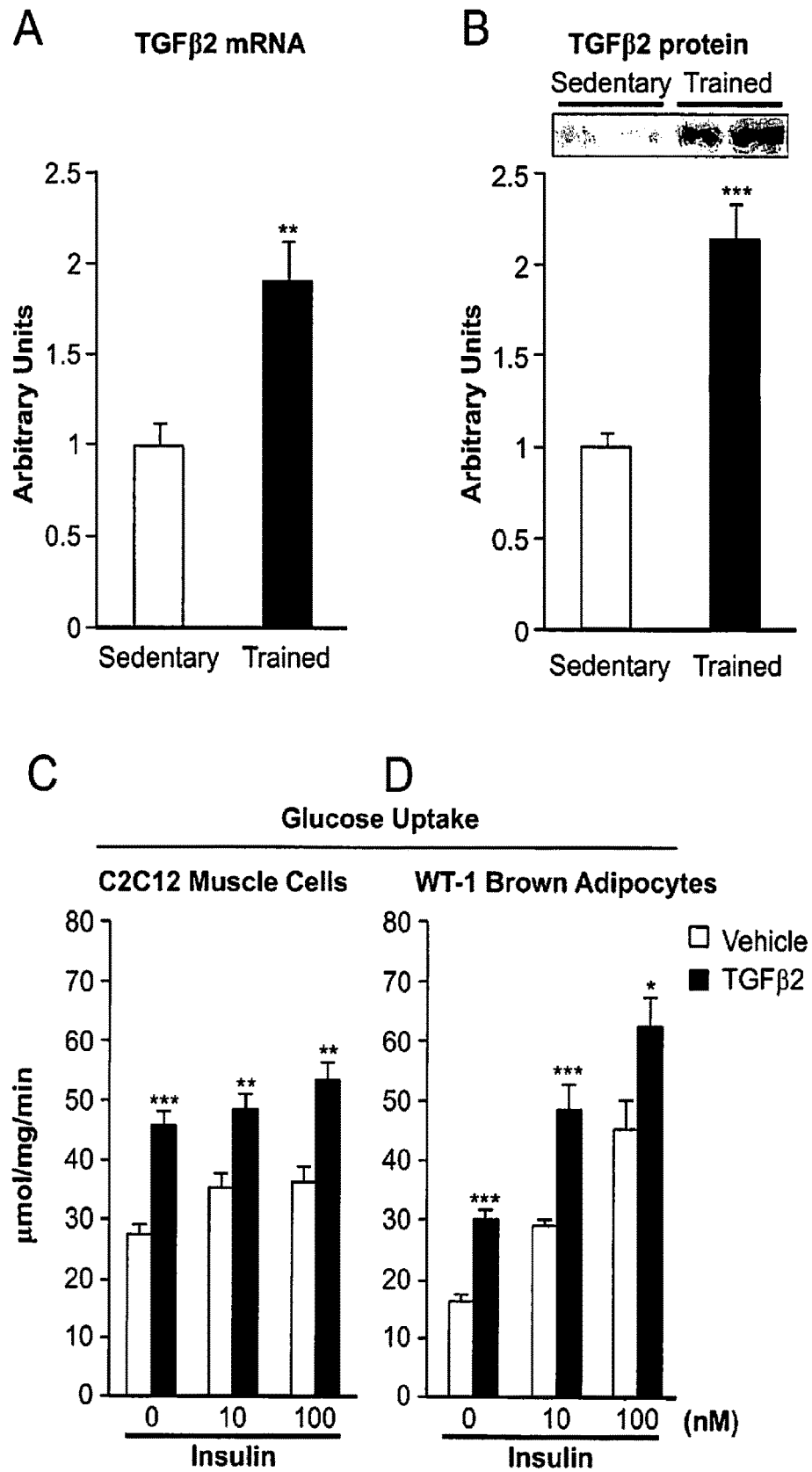
FIG. 5 shows that exercise training increases TGFβ2 mRNA and protein, and TGFβ2 recombinant protein increases glucose uptake. (A), (B) Mice were housed in static cages (Sedentary, N=5) or in wheel cages for 11 days (Trained, N=5). mRNA (A) and protein (B) were measured in scWAT, p<0.01, *p<0.001 vs. sedentary. Differentiated C2C12 Muscel Cells (C), and WT-1 Brown Adipocytes (D), were incubated with vehicle or TGFβ2 (20 mg/ml) for 20 hrs in complete DMEM and then (−) FBS for 4 hrs. 2-deoxy-D-[3H] glucose uptake was measured and normalized for protein content. N=3 in duplicate, *p<0.05, p, 0.01, *p, 0.001 vs. vehicle.

Incubation of Cultured Muscle Cells and Adipocytes with CRISP-1, APOM, BCAN, and TCN2 Increase Glucose Uptake and Fatty Acid Uptake and Oxidation Transplantation of trained scWAT increases glucose uptake in skeletal muscle and brown adipose tissue in recipient mice. Recently, we have generated exciting preliminary data showing that TGFβ2 increases glucose uptake in muscle and fat cells (FIG. 5), findings that also indicate that a protein secreted from trained scWAT may mediate the effects of transplantation on tissue glucose uptake and systemic glucose homeostasis. In this experiment it will be determine if the other candidate adipokines also increase glucose uptake, as well as determine if incubation of cells with all of these proteins increase fatty acid oxidation.

It will be shown that exercise training-induced scWAT adipokines increase glucose uptake and fatty acid uptake and oxidation in cultured muscle cells and brown adipocytes.

Experimental Methods:

Glucose uptake and glucose transporter expression (GLUT1/4) in C2C12 muscle cells and WT-1 brown adipocytes will be measured as described above. Recombinant proteins have (or will be) purchased from commercial sources [TGFβ2 (Cell Signaling 8406), CRISP-1(Abnova; H00000167-P01), APOM (syd labs; BP000056-CYT-715), BCAN (R&D systems; 7188-BC-050), TCN2 (Abnova; H00006948-P02)]. Cells will be incubated in the presence or absence of selected proteins at various concentrations. Incubation times will range from 30 min for study of short term effects and up to 48 hours to determine long term effects. Glucose uptake will be measured in the basal state, with submaximal and maximal insulin. Fatty acid uptake and oxidation will be measured with $[1-^{14}C]$ palmitate as we (89) and others (90,91) have used.

Alternative Approach:

Depending on the outcome of the cell experiments, we may measure the effects of TGFβ2, CRISP-1, APOM, BCAN, and/or TCN2 incubation on glucose uptake, fatty acid uptake, and fatty acid oxidation in isolated skeletal muscles. If the candidate adipokines stimulate metabolism in isolated muscles, this would provide more support for the in vivo studies described in prophetic Experiment. 3d. Isolated muscles could also define the mechanism of action through the measurement of intracellular signaling and transcriptional events.

Experiment 3d

In Vivo Treatment of Mice with TGFβ2, CRISP-1, APOM, BCAN, and TCN2 Improves Systemic and Peripheral Metabolism in Mice It will be shown that treatment of mice with these candidate adipokines will improve systemic and tissue metabolism.

Experimental Methods:

Recombinant adenoviral vectors will be prepared by the MassGeneral Vector Core (Charlestown, Mass.). Virus will be injected through the tail vein, resulting in overexpression and secretion from liver. By this method, sufficient amounts of recombinant protein should be expressed (5). Male mice (12 wk) will be studied at 2, 9, 14, or 28 days following injection. To study whole-body glucose homeostasis, mice will undergo glucose and insulin tolerance tests, euglycemic-hyperinsulinemic clamp studies, circulating insulin, triglycerides, free fatty acids, cholesterol, and several established adipokines. Mice will also be housed in metabolic chambers to assess energy expenditure, physical activity, RER, etc. To determine if the adipokines have tissue-specific effects, skeletal muscles, brown adipose tissue, and liver will be obtained from the treated mice and used to measure glucose uptake, fatty acid uptake and oxidation, intracellular signaling pathways, and the expression and/or activity of key metabolic proteins, as described throughout this application. If one or more novel adipokines are effective in increasing or decreasing glucose homeostasis, adipokines will next be tested using animal models of obesity and diabetes, such as the high-fat fed mouse. These experiments will demonstrate the effects of the novel adipokines on systemic and tissue metabolic homeostasis.

CITED REFERENCES

1. Vernochet C, Mourier A, Bezy O, Macotela Y, Boucher J, Rardin M J, An D, Lee K Y, Ilkayeva O R, Zingaretti C M, Emanuelli B, Smyth G, Cinti S, Newgard C B, Gibson B W, Larsson N G, Kahn C R: Adipose-specific deletion of TFAM increases mitochondrial oxidation and protects mice against obesity and insulin resistance. *Cell Metab.* 16:765-776, 2012
2. Pedersen L, Hojman P: Muscle-to-organ cross talk mediated by myokines. *Adipocyte.* 1:164-167, 2012
3. Pedersen B K, Febbraio M A: Muscles, exercise and obesity: skeletal muscle as a secretory organ. *Nat Rev Endocrinol.* 8:457-465, 2012
4. Brandt C, Jakobsen A H, Adser H, Olesen J, Iversen N, Kristensen J M, Hojman P, Wojtaszewski J F, Hidalgo J, Pilegaard H: IL-6 regulates exercise and training-induced adaptations in subcutaneous adipose tissue in mice. *Acta Physiol (Oxf).* 205:224-235, 2012
5. Bostrom P, Wu J, Jedrychowski M P, Korde A, Ye L, Lo J C, Rasbach K A, Bostrom E A, Choi J H, Long J Z, Kajimura S, Zingaretti M C, Vind B F, Tu H, Cinti S, Hojlund K, Gygi S P, Spiegelman B M: A PGC1-alpha-dependent myokine that drives brown-fat-like development of white fat and thermogenesis. *Nature.* 481:463-468, 2012
6. Moreno-Navarrete J M, Ortega F, Serrano M, Guerra E, Pardo G, Tinahones F, Ricart W, Fernandez-Real J M: Irisin is expressed and produced by human muscle and adipose tissue in association with obesity and insulin resistance. *J Clin Endocrinol Metab.* 98:E769-E778, 2013
7. Shan T, Liang X, Bi P, Kuang S: Myostatin knockout drives browning of white adipose tissue through activating the AMPK-PGC1alpha-Fndc5 pathway in muscle. *FASEB J.* 27:1981-1989, 2013
8. Huh J Y, Panagiotou G, Mougios V, Brinkoetter M, Vamvini M T, Schneider B E, Mantzoros C S: FNDC5 and irisin in humans: I. Predictors of circulating concentrations in serum and plasma and II. mRNA expression and circulating concentrations in response to weight loss and exercise. *Metabolism.* 61:1725-1738, 2012
9. Graham T E, Brandauer J, Oberbach A, Bluher M, Goodyear L J, Kahn B B: RBP4 expression in skeletal muscle correlates highly with Insulin Resistance and is Differentially Regulated by Exercise in Normal Versus Insulin Resistant Subjects. *Diabetes* 56: A38, 2007
10. Boyle J P, Thompson T J, Gregg E W, Barker L E, Williamson D F: Projection of the year 2050 burden of diabetes in the US adult population: dynamic modeling of incidence, mortality, and prediabetes prevalence. *Popul. Health Metr.* 8:29:29, 2010
11. Overweight, obesity, and health risk. National Task Force on the Prevention and Treatment of Obesity. *Arch. Intern. Med.* 160:898-904, 2000
12. Harris M I, Flegal K M, Cowie C C, Eberhardt M S, Goldstein D E, Little R R, Wiedmeyer H M, Byrd-Holt D D: Prevalence of diabetes, impaired fasting glucose, and impaired glucose tolerance in U.S. adults. The Third National Health and Nutrition Examination Survey, 1988-1994. *Diabetes Care.* 21:518-524, 1998
13. DeFronzo R A, Jacot E, Jequier E, Maeder E, Wahren J, Felber J P: The effect of insulin on the disposal of intravenous glucose. Results from indirect calorimetry and hepatic and femoral venous catheterization. *Diabetes* 30:1000-1007, 1981
14. Knowler W C, Barrett-Connor E, Fowler S E, Hamman R F, Lachin J M, Walker E A, Nathan D M: Reduction in the incidence of Type 2 diabetes with lifestyle intervention or metformin. *N Engl J Med* 346:393-403, 2002
15. Bonadonna R C, Del Prato S, Saccomani M P, Bonora E, Gulli G, Ferrannini E, Bier D, Cobelli C, DeFronzo R A: Transmembrane glucose transport in skeletal muscle of patients with non-insulin-dependent diabetes. *J. Clin. Invest.* 92:486-494, 1993
16. Tran T T, Kahn C R: Transplantation of adipose tissue and stem cells: role in metabolism and disease. *Nat Rev Endocrinol.* 6:195-213, 2010
17. Carey V J, Walters E E, Colditz G A, Solomon C G, Willett W C, Rosner B A, Speizer F E, Manson J E: Body fat distribution and risk of non-insulin-dependent diabetes mellitus in women. The Nurses' Health Study. *Am. J. Epidemiol.* 145:614-619, 1997
18. Wang Y, Rimm E B, Stampfer M J, Willett W C, Hu F B: Comparison of abdominal adiposity and overall obesity in predicting risk of type 2 diabetes among men. *Am J Clin Nutr.* 81:555-563, 2005
19. Zhang C, Rexrode K M, van Dam Rm, Li T Y, Hu F B: Abdominal obesity and the risk of all-cause, cardiovascular, and cancer mortality: sixteen years of follow-up in US women. *Circulation.* 117:1658-1667, 2008
20. Misra A, Garg A, Abate N, Peshock R M, Stray-Gundersen J, Grundy S M: Relationship of anterior and posterior subcutaneous abdominal fat to insulin sensitivity in nondiabetic men. *Obes Res.* 5:93-99, 1997
21. Snijder M B, Dekker J M, Visser M, Bouter L M, Stehouwer C D, Kostense P J, Yudkin J S, Heine R J, Nijpels G, Seidell J C: Associations of hip and thigh circumferences independent of waist circumference with the incidence of type 2 diabetes: the Hoorn Study. *Am J Clin Nutr.* 77:1192-1197, 2003

22. Torriani M, Fitch K, Stavrou E, Bredella M A, Lim R, Sass C A, Cypess A M, Grinspoon S: Deiodinase 2 expression is increased in dorsocervical fat of patients with HIV-associated lipohypertrophy syndrome. *J Clin Endocrinol Metab.* 97:E602-E607, 2012

23. Vosselman M J, Marken Lichtenbelt W D, Schrauwen P: Energy dissipation in brown adipose tissue: From mice to men. *Mol Cell Endocrinol.* 10, 2013

24. Cannon B, Houstek J, Nedergaard J: Brown adipose tissue. More than an effector of thermogenesis? *Ann. NY. Acad Sci.* 856:171-87:171-187, 1998

25. Rothwell N J, Stock M J: Effects of age on diet-induced thermogenesis and brown adipose tissue metabolism in the rat. *Int J Obes.* 7:583-589, 1983

26. Marken Lichtenbelt W D, Vanhommerig J W, Smulders N M, Drossaerts J M, Kemerink G J, Bouvy N D, Schrauwen P, Teule G J: Cold-activated brown adipose tissue in healthy men. *N Engl. J Med.* 360:1500-1508, 2009

27. Lowell B B, Susulic V, Hamann A, Lawitts J A, Himms-Hagen J, Boyer B B, Kozak L P, Flier J S: Development of obesity in transgenic mice after genetic ablation of brown adipose tissue. *Nature.* 366:740-742, 1993

28. Bartelt A, Bruns O T, Reimer R, Hohenberg H, Ittrich H, Peldschus K, Kaul M G, Tromsdorf U I, Weller H, Waurisch C, Eychmuller A, Gordts P L, Rinninger F, Bruegelmann K, Freund B, Nielsen P, Merkel M, Heeren J: Brown adipose tissue activity controls triglyceride clearance. *Nat Med.* 17:200-205, 2011

29. Guerra C, Koza R A, Yamashita H, Walsh K, Kozak L P: Emergence of brown adipocytes in white fat in mice is under genetic control. Effects on body weight and adiposity. *J Clin Invest.* 102:412-420, 1998

30. Dulloo A G, Miller D S: Energy balance following sympathetic denervation of brown adipose tissue. *Can J Physiol Pharmacol.* 62:235-240, 1984

31. Enerback S: The origins of brown adipose tissue. *N Engl. J Med.* 360:2021-2023, 2009

32. Spiegelman B M: Banting lecture 2012: regulation of adipogenesis: toward new therapeutics for metabolic disease. *Diabetes.* 62:1774-1782, 2013

33. Lidell M E, Betz M J, Dahlqvist L O, Heglind M, Elander L, Slawik M, Mussack T, Nilsson D, Romu T, Nuutila P, Virtanen K A, Beuschlein F, Persson A, Borga M, Enerback S: Evidence for two types of brown adipose tissue in humans. *Nat Med.* 19:631-634, 2013

34. Petrovic N, Walden T B, Shabalina I G, Timmons J A, Cannon B, Nedergaard J: Chronic peroxisome proliferator-activated receptor gamma (PPARgamma) activation of epididymally derived white adipocyte cultures reveals a population of thermogenically competent, UCP1-containing adipocytes molecularly distinct from classic brown adipocytes. *J Biol Chem.* 285:7153-7164, 2010

35. Ishibashi J, Seale P: Medicine. Beige can be slimming. *Science.* 328:1113-1114, 2010

36. Wu J, Bostrom P, Sparks L M, Ye L, Choi J H, Giang A H, Khandekar M, Virtanen K A, Nuutila P, Schaart G, Huang K, Tu H, Marken Lichtenbelt W D, Hoeks J, Enerback S, Schrauwen P, Spiegelman B M: Beige adipocytes are a distinct type of thermogenic fat cell in mouse and human. *Cell.* 150:366-376, 2012

37. Hirshman M F, Wardzala L J, Goodyear L J, Fuller S P, Horton E D, Horton E S: Exercise training increases the number of glucose transporters in rat adipose cells. *Am. J. Physiol.* 257:E520-E530, 1989

38. Gollisch K S, Brandauer J, Jessen N, Toyoda T, Nayer A, Hirshman M F, Goodyear L J: Effects of exercise training on subcutaneous and visceral adipose tissue in normal- and high-fat diet-fed rats. *Am. J. Physiol Endocrinol. Metab.* 297:E495-E504, 2009

39. Ruschke K, Fishbein L, Dietrich A, Kloting N, Tonjes A, Oberbach A, Fasshauer M, Jenkner J, Schon M R, Stumvoll M, Bluher M, Mantzoros C S: Gene expression of PPARgamma and PGC-1alpha in human omental and subcutaneous adipose tissues is related to insulin resistance markers and mediates beneficial effects of physical training. *Eur. J. Endocrinol.* 162:515-523, 2010

40. Bradley R L, Jeon J Y, Liu F F, Maratos-Flier E: Voluntary exercise improves insulin sensitivity and adipose tissue inflammation in diet-induced obese mice. *Am. J. Physiol Endocrinol. Metab.* 295:E586-E594, 2008

41. Tran T T, Yamamoto Y, Gesta S, Kahn C R: Beneficial effects of subcutaneous fat transplantation on metabolism. *Cell Metab.* 7:410-420, 2008

42. Pavlou M P, Diamandis E P: The cancer cell secretome: a good source for discovering biomarkers? *J Proteomics.* 73:1896-1906, 2010

43. Skalnikova H, Motlik J, Gadher S J, Kovarova H: Mapping of the secretome of primary isolates of mammalian cells, stem cells and derived cell lines. *Proteomics.* 11:691-708, 2011

44. Rabe K, Lehrke M, Parhofer K G, Broedl U C: Adipokines and insulin resistance. *Mol Med.* 14:741-751, 2008

45. Hauner H: Secretory factors from human adipose tissue and their functional role. *Proc Nutr Soc.* 64:163-169, 2005

46. Halberg N, Wernstedt-Asterholm I, Scherer P E: The adipocyte as an endocrine cell. *Endocrinol Metab Clin North Am.* 37:753-7xi, 2008

47. Bluher M, Williams C J, Kloting N, Hsi A, Ruschke K, Oberbach A, Fasshauer M, Berndt J, Schon M R, Wolk A, Stumvoll M, Mantzoros C S: Gene expression of adiponectin receptors in human visceral and subcutaneous adipose tissue is related to insulin resistance and metabolic parameters and is altered in response to physical training. *Diabetes Care.* 30:3110-3115, 2007

48. Christiansen T, Paulsen S K, Bruun J M, Ploug T, Pedersen S B, Richelsen B: Diet-induced weight loss and exercise alone and in combination enhance the expression of adiponectin receptors in adipose tissue and skeletal muscle, but only diet-induced weight loss enhanced circulating adiponectin. *J Clin Endocrinol Metab.* 95:911-919, 2010

49. Polak J, Klimcakova E, Moro C, Viguerie N, Berlan M, Hejnova J, Richterova B, Kraus I, Langin D, Stich V: Effect of aerobic training on plasma levels and subcutaneous abdominal adipose tissue gene expression of adiponectin, leptin, interleukin 6, and tumor necrosis factor alpha in obese women. *Metabolism.* 55:1375-1381, 2006

50. Klimcakova E, Polak J, Moro C, Hejnova J, Majercik M, Viguerie N, Berlan M, Langin D, Stich V: Dynamic strength training improves insulin sensitivity without altering plasma levels and gene expression of adipokines in subcutaneous adipose tissue in obese men. *J Clin Endocrinol Metab.* 91:5107-5112, 2006

51. Leick L, Lindegaard B, Stensvold D, Plomgaard P, Saltin B, Pilegaard H: Adipose tissue interleukin-18 mRNA and plasma interleukin-18: effect of obesity and exercise. *Obesity* (Silver.Spring). 15:356-363, 2007

52. Stolic M, Russell A, Nutley L, Fielding G, Hay J, MacDonald G, Whitehead J, Prins J: Glucose uptake and insulin action in human adipose tissue—influence of BMI, anatomical depot and body fat distribution. *Int J Obes Relat Metab Disord.* 26:17-23, 2002

53. Tanko L B, Bagger Y Z, Alexandersen P, Larsen P J, Christiansen C: Central and peripheral fat mass have contrasting effect on the progression of aortic calcification in postmenopausal women. *Eur Heart J.* 24:1531-1537, 2003

54. Ho R C, Alcazar O, Fujii N, Hirshman M F, Goodyear L J: p38{gamma} MAPK regulation of glucose transporter expression and glucose uptake in L6 myotubes and mouse skeletal muscle. *Am. J Physiol Regul. Integr. Comp Physiol* 286:R342-R349, 2004

55. Kramer H F, Taylor E B, Witczak C A, Fujii N, Hirshman M F, Goodyear L J: The calmodulin-binding domain of AS160 regulates contraction—but not insulin-stimulated glucose uptake in skeletal muscle. *Diabetes.* 56:2854-2862, 2007

56. Witczak C A, Jessen N, Warro D M, Toyoda T, Fujii N, Anderson M E, Hirshman M F, Goodyear L J: CaMKII regulates contraction—but not insulin-induced glucose uptake in mouse skeletal muscle. *Am J Physiol Endocrinol Metab* 298:E1150-E1160, 2010

57. Ariano M A, Armstrong R B, Edgerton V R: Hindlimb muscle fiber populations of five mammals. *J. Histochem. Cytochem.* 21:51-55, 1973

58. Bertrand A, Ngo-Muller V, Hentzen D, Concordet J P, Daegelen D, Tuil D: Muscle electrotransfer as a tool for studying muscle fiber-specific and nerve-dependent activity of promoters. *Am. J Physiol Cell Physiol* 285:C1071-C1081, 2003

59. Mahoney D J, Parise G, Melov S, Safdar A, Tarnopolsky M A: Analysis of global mRNA expression in human skeletal muscle during recovery from endurance exercise. *FASEB J.* 19:1498-1500, 2005

60. Fu L, Liu X, Niu Y, Yuan H, Zhang N, Lavi E: Effects of high-fat diet and regular aerobic exercise on global gene expression in skeletal muscle of C57BL/6 mice. *Metabolism.* 61:146-152, 2012

61. Choi S, Liu X, Li P, Akimoto T, Lee S Y, Zhang M, Yan Z: Transcriptional profiling in mouse skeletal muscle following a single bout of voluntary running: evidence of increased cell proliferation. *J Appl Physiol.* 99:2406-2415, 2005

62. Keller P, Vollaard N B, Gustafsson T, Gallagher I J, Sundberg C J, Rankinen T, Britton S L, Bouchard C, Koch L G, Timmons J A: A transcriptional map of the impact of endurance exercise training on skeletal muscle phenotype. *J Appl Physiol.* 110:46-59, 2011

63. Cao L, Choi E Y, Liu X, Martin A, Wang C, Xu X, During M J: White to brown fat phenotypic switch induced by genetic and environmental activation of a hypothalamic-adipocyte axis. *Cell Metab.* 14:324-338, 2011

64. Pardo M, Roca-Rivada A, Seoane L M, Casanueva F F: Obesidomics: contribution of adipose tissue secretome analysis to obesity research. *Endocrine.* 41:374-383, 2012

65. Thompson D, Karpe F, Lafontan M, Frayn K: Physical activity and exercise in the regulation of human adipose tissue physiology. *Physiol Rev.* 92:157-191, 2012

66. Nielsen L B, Christoffersen C, Ahnstrom J, Dahlback B: ApoM: gene regulation and effects on HDL metabolism. *Trends Endocrinol Metab.* 20:66-71, 2009

67. Wirrig E E, Snarr B S, Chintalapudi M R, O'neal J L, Phelps A L, Barth J L, Fresco V M, Kern C B, Mjaatvedt C H, Toole B P, Hoffman S, Trusk T C, Argraves W S, Wessels A: Cartilage link protein 1 (Crtl1), an extracellular matrix component playing an important role in heart development. *Dev. Biol.* 310:291-303, 2007

68. Clark D A, Coker R: Transforming growth factor-beta (TGF-beta). *Int J Biochem Cell Biol.* 30:293-298, 1998

69. Reddy T, Gibbs G M, Merriner D J, Kerr J B, O'Bryan M K: Cysteine-rich secretory proteins are not exclusively expressed in the male reproductive tract. *Dev. Dyn.* 237:3313-3323, 2008

70. Sanford L P, Ormsby I, Gittenberger-de Groot A C, Sariola H, Friedman R, Boivin G P, Cardell E L, Doetschman T: TGFbeta2 knockout mice have multiple developmental defects that are non-overlapping with other TGFbeta knockout phenotypes. *Development.* 124:2659-2670, 1997

71. Nakazaki H, Shen Y W, Yun B, Reddy A, Khanna V, Mania-Farnell B, Ichi S, McLone D G, Tomita T, Mayanil C S: Transcriptional regulation by Pax3 and TGFbeta2 signaling: a potential gene regulatory network in neural crest development. *Int J Dev. Biol.* 53:69-79, 2009

72. Fuchshofer R, Tamm E R: The role of TGF-beta in the pathogenesis of primary open-angle glaucoma. *Cell Tissue Res.* 347:279-290, 2012

73. Qu X, Zhao S, Gao J, Hu M, Dong L, Zhang X: [Reduced expression and secretion of apolipoprotein M in fat-fed, streptozotocin-diabetic rats is partially reversed by an artificial ligand of PPARgamma]. *Zhong. Nan. Da. Xue. Xue. Bao. Yi. Xue. Ban.* 37:796-801, 2012

74. Koh H J, Arnolds D E, Fujii N, Tran T T, Rogers M J, Jessen N, Li Y, Liew C W, Ho R C, Hirshman M F, Kulkarni R N, Kahn C R, Goodyear L J: Skeletal muscle-selective knockout of LKB1 increases insulin sensitivity, improves glucose homeostasis, and decreases TRB3. *Mol Cell Biol.* 26:8217-8227, 2006

75. Higaki Y, Wojtaszewski J F P, Hirshman M F, Withers D J, Towery H, White M F, Goodyear L J: Insulin receptor substrate-2 is not necessary for insulin- and exercise-stimulated glucose transport in skeletal muscle. *J Biol. Chem.* 274:20791-20795, 1999

76. Sakamoto K, Arnolds D E, Fujii N, Kramer H F, Hirshman M F, Goodyear L J: Role of Akt2 in contraction-stimulated cell signaling and glucose uptake in skeletal muscle. *Am J Physiol Endocrinol. Metab.* 291:E1031-E1037, 2006

77. Goodyear L J, Giorgino F, Sherman L A, Carey J, Smith R J, Dohm G L: Insulin receptor phosphorylation, insulin receptor substrate-1 phosphorylation, and phosphatidylinositol 3-kinase activity are decreased in intact skeletal muscle strips from obese subjects. *J. Clin. Invest.* 95:2195-2204, 1995

78. Goodyear L J, Giorgino F, Balon T W, Condorelli G, Smith R J: Effects of contractile activity on tyrosine phophoproteins and PI 3-kinase activity in rat skeletal muscle. *Am. J. Physiol.* 268:E987-E995, 1995

79. Kramer H F, Witczak C A, Taylor E B, Fujii N, Hirshman M F, Goodyear L J: AS160 regulates insulin- and contraction-stimulated glucose uptake in mouse skeletal muscle. *J Biol. Chem.* 281:31478-85, 2006

80. Taylor E B, An D, Kramer H F, Yu H, Fujii N L, Roeckl K S, Bowles N, Hirshman M F, Xie J, Feener E P, Goodyear L J: Discovery of TBC1 D1 as an Insulin-, AICAR-, and Contraction-stimulated Signaling Nexus in Mouse Skeletal Muscle. *J Biol. Chem.* 283:9787-9796, 2008

81. Röckl K S, Hirshman M F, Brandauer J, Fujii N, Witters L A, Goodyear L J: Skeletal Muscle Adaptation to Exer- 81. cise Training: AMP-Activated Protein Kinase Mediates Muscle Fiber Type Shift. *Diabetes.* 56:2062-2069, 2007
82. Fujii N, Ho R C, Manabe Y, Jessen N, Toyoda T, Holland W L, Summers S A, Hirshman M F, Goodyear L J: Ablation of AMP-activated protein kinase alpha2 activity exacerbates insulin resistance induced by high-fat feeding of mice. *Diabetes.* 57:2958-2966, 2008
83. Barre L, Richardson C, Hirshman M F, Brozinick J, Fiering S, Kemp B E, Goodyear L J, Witters L A: Genetic model for the chronic activation of skeletal muscle AMP-activated protein kinase leads to glycogen accumulation. *Am J Physiol Endocrinol. Metab.* 292:E802-E811, 2007
84. Talmadge R J, Roy R R: Electrophoretic separation of rat skeletal muscle myosin heavy-chain isoforms. *J. Appl. Physiol* 75:2337-2340, 1993
85. Ceglia L, da Silva M M, Park L K, Morris E, Harris S S, Bischoff-Ferrari H A, Fielding R A, Dawson-Hughes B: Multi-step immunofluorescent analysis of vitamin D receptor loci and myosin heavy chain isoforms in human skeletal muscle. *J Mol Histol.* 41:137-142, 2010
86. Guo L, Burke P, Lo S H, Gandour-Edwards R, Lau D: Quantitative analysis of angiogenesis using confocal laser scanning microscopy. *Angiogenesis.* 4:187-191, 2001
87. Waters R E, Rotevatn S, Li P, Annex B H, Yan Z: Voluntary running induces fiber type-specific angiogenesis in mouse skeletal muscle. *Am J Physiol Cell Physiol.* 287:01342-01348, 2004
88. Augustus A S, Kako Y, Yagyu H, Goldberg I J: Routes of F A delivery to cardiac muscle: modulation of lipoprotein lipolysis alters uptake of T G-derived F A. *Am J Physiol Endocrinol Metab.* 284:E331-E339, 2003
89. Norris A W, Hirshman M F, Yao J, Jessen N, Musi N, Chen I, Sivitz W I, Goodyear L J, Kahn C R: Endogenous peroxisome proliferator-activated receptor-gamma augments fatty acid uptake in oxidative muscle. *Endocrinology.* 149:5374-5383, 2008
90. Dyck D J, Bonen A: Muscle contraction increases palmitate esterification and oxidation and triacylglycerol oxidation. *Am J Physiol.* 275:E888-E896, 1998
91. Steinberg G R, Bonen A, Dyck D J: Fatty acid oxidation and triacylglycerol hydrolysis are enhanced after chronic leptin treatment in rats. *Am J Physiol Endocrinol. Metab.* 282:E593-E600, 2002
92. Zhou G, Myers R, Li Y, Chen Y, Shen X, Fenyk-Melody J, Wu M, Ventre J, Doebber T, Fujii N, Musi N, Hirshman M F, Goodyear L J, Moller D E: Role of AMP-activated protein kinase in mechanism of metformin action. *J Clin. Invest* 108:1167-1174, 2001
93. Kuhl J E, Ruderman N B, Musi N, Goodyear L J, Patti M E, Crunkhorn S, Dronamraju D, Thorell A, Nygren J, Ljungkvist O, Degerblad M, Stahle A, Brismar T B, Saha A K, Efendic S, Bavenholm P N: Exercise training decreases the concentration of malonyl CoA and increases the expression and activity of malonyl CoA decarboxylase in human muscle. *Am J Physiol Endocrinol. Metab.* 290:E1296-303, 2006
94. Weigle D S, Hutson A M, Kramer J M, Fallon M G, Lehner J M, Lok S, Kuijper J L: Leptin does not fully account for the satiety activity of adipose tissue-conditioned medium. *Am J Physiol.* 275:R976-R985, 1998
95. Rodbell M: Metabolism of isolated fat cells. I. Effects of hormones on glucose metabolism and lipolysis. *J. Biol. Chem.* 239:375-380, 1964
96. Cushman S W: Structure-function relationship in the adipose cell. I Ultrastructure of the isolated adipose cell. *J. Cell Biol.* 46:326-341, 1970
97. Townsend K L, An D, Lynes M D, Huang T L, Zhang H, Goodyear L J, Tseng Y H: Increased Mitochondrial Activity in BMP7-treated Brown Adipocytes, Due to Increased CPT1- and CD36-mediated Fatty Acid Uptake. *Antioxid. Redox. Signal.* 19:243-57, 2013
98. Cushman S W, Heindel J J, Jeanrenaud B: Cell-associated nonesterified fatty acid levels and their alteration during lipolysis in the isolated mouse adipose cell. *J Lipid. Res.* 14:632-642, 1973
99. Wu M, Neilson A, Swift A L, Moran R, Tamagnine J, Parslow D, Armistead S, Lemire K, Orrell J, Teich J, Chomicz S, Ferrick D A: Multiparameter metabolic analysis reveals a close link between attenuated mitochondrial bioenergetic function and enhanced glycolysis dependency in human tumor cells. *Am J Physiol Cell Physiol.* 292:0125-0136, 2007
100. Kiefer F W, Vernochet C, O'Brien P, Spoerl S, Brown J D, Nallamshetty S, Zeyda M, Stulnig T M, Cohen D E, Kahn C R, Plutzky J: Retinaldehyde dehydrogenase 1 regulates a thermogenic program in white adipose tissue. *Nat Med.* 18:918-925, 2012
101. Tseng Y H, Cypess A M, Kahn C R: Cellular bioenergetics as a target for obesity therapy. *Nat Rev Drug Discov.* 9:465-482, 2010
102. Kim J K: Hyperinsulinemic-euglycemic clamp to assess insulin sensitivity in vivo. *Methods Mol Biol.* 560:221-38:221-238, 2009
103. Le Marchand Y, Singh A, Assimacopoulos-Jeannet F, orci I, Rouiller C, Jeanrenaud B: A role for the microtubular system in the release of very low density lipoproteins by perfused mouse livers. *J Biol. Chem.* 248:6862-6870, 1973
104. Perry D K, Bielawska A, Hannun Y A: Quantitative determination of ceramide using diglyceride kinase. *Methods. Enzymol.* 312:22-31:22-31, 2000
105. Ong K T, Mashek M T, Bu S Y, Greenberg A S, Mashek D G: Adipose triglyceride lipase is a major hepatic lipase that regulates triacylglycerol turnover and fatty acid signaling and partitioning. *Hepatology.* 53:116-126, 2011
106. Fujii N, Boppart M D, Dufresne S D, Crowley P F, Jozsi A C, Sakamoto K, Yu H, Aschenbach W G, Kim S, Miyazaki H, Rui L, White M F, Hirshman M F, Goodyear L J: Overexpression or ablation of JNK in skeletal muscle has no effect on glycogen synthase activity. *Am J Physiol Cell Physiol* 287:C200-C208, 2004
107. Seglen P O: Preparation of isolated rat liver cells. *Methods Cell Biol.* 13:29-83:29-83, 1976
108. Sakamoto K, Hirshman M F, Aschenbach W G, Goodyear L J: Contraction regulation of Akt in rat skeletal muscle. *J Biol. Chem.* 277:11910-11917, 2002
109. Wang Z, Zhu T, Qiao C, Zhou L, Wang B, Zhang J, Chen C, Li J, Xiao X: Adeno-associated virus serotype 8 efficiently delivers genes to muscle and heart. *Nat Biotechnol.* 23:321-328, 2005

What is claimed is:

1. A method of positively modulating glycemic control in a subject, said method comprising: administering to a subject in need of positive modulation of glycemic control one or more factors, wherein said factors are selected from the group consisting of a factor consisting of transforming growth factor beta 2 (TGFP2) and a factor consisting of trancobalamin 2 (TCN2), in an amount suitable for positively modulating glycemic control thereby effecting a positive modulation of glycemic control in the subject.

2. The method of claim 1, wherein the method additionally comprises detecting a positive modulating effect on glycemic control in the subject.

3. The method of claim 1, wherein the positive modulating effect of the factor is determined by comparing the glycemic control of treated subjects with the glycemic control of subjects not in need of glycemic modulation.

4. The method of claim 1, wherein the positive modulating effect of the factor is determined by comparing the blood glucose level of the subject with the known accepted range for a subject not in need of glycemic control.

5. The method of claim 1, wherein said subject in need of glycemic control has diabetes.

6. The method of claim 5, wherein said subject has type 2 diabetes.

7. The method of claim 1, wherein said positive modulating effect of the factor is determined by comparing the effect of the administered factor on glucose metabolism before and after treatment.

8. The method of claim 7, wherein said determination of the positive modulation of glycemic control is made by measuring blood glucose levels over time.

9. The method of claim 3, wherein glycemic control is determined by a standard glucose tolerance test or standard glucose intolerance test.

10. The method of claim 1, wherein said factor is a factor consisting of transforming growth factor beta 2 (TGFP2).

* * * * *

UNITED STATES PATENT AND TRADEMARK OFFICE
CERTIFICATE OF CORRECTION

PATENT NO.         : 10,632,175 B2
APPLICATION NO.    : 14/771677
DATED              : April 28, 2020
INVENTOR(S)        : Laurie J. Goodyear et al.

It is certified that error appears in the above-identified patent and that said Letters Patent is hereby corrected as shown below:

In the Claims

Column 38; Claim 1; Line 6 - please amend:
"growth factor beta 2 (TGFP2) and a factor consisting of"

To:
--growth factor beta 2 (TGFβ2) and a factor consisting of--

Column 39; Claim 10; Line 2 - please amend:
"consisting of transforming growth factor beta 2 (TGFP2)."

To:
--consisting of transforming growth factor beta 2 (TGFβ2).--

Signed and Sealed this
First Day of December, 2020

Andrei Iancu
*Director of the United States Patent and Trademark Office*